US012751826B2

(12) United States Patent
Troxell et al.

(10) Patent No.: US 12,751,826 B2
(45) Date of Patent: Oct. 6, 2026

(54) SMART IMPLANTS FOR PERIPROSTHETIC JOINT INFECTION

(71) Applicant: GLOBUS MEDICAL, INC., Audubon, PA (US)

(72) Inventors: Paden Troxell, Conshohocken, PA (US); David C. Paul, Phoenixville, PA (US)

(73) Assignee: Globus Medical Inc., Audubon, PA (US)

( * ) Notice: Subject to any disclaimer, the term of this patent is extended or adjusted under 35 U.S.C. 154(b) by 489 days.

(21) Appl. No.: 18/455,696

(22) Filed: Aug. 25, 2023

(65) Prior Publication Data

US 2025/0064590 A1 Feb. 27, 2025

(51) Int. Cl.

| | |
|---|---|
| ***A61B 5/00*** | (2006.01) |
| ***A61F 2/30*** | (2006.01) |
| ***A61F 2/48*** | (2006.01) |
| ***A61N 1/08*** | (2006.01) |
| ***A61N 1/32*** | (2006.01) |
| *A61F 2/38* | (2006.01) |

(52) U.S. Cl.

CPC .............. *A61F 2/30* (2013.01); *A61B 5/0031* (2013.01); *A61B 5/412* (2013.01); *A61B 5/4528* (2013.01); *A61B 5/4839* (2013.01); *A61F 2/482* (2021.08); *A61N 1/08* (2013.01); *A61N 1/32* (2013.01); *A61F 2002/30668* (2013.01); *A61F 2/3877* (2013.01)

(58) Field of Classification Search

CPC ..... A61B 5/4851; A61B 5/0031; A61B 5/686; A61B 5/057; A61B 5/4839; A61F 2/482; A61N 1/08

See application file for complete search history.

(56) References Cited

U.S. PATENT DOCUMENTS

| | | | |
|---|---|---|---|
| 4,150,293 | A | 4/1979 | Franke |
| 5,246,010 | A | 9/1993 | Gazzara et al. |
| 5,354,314 | A | 10/1994 | Hardy et al. |
| 5,397,323 | A | 3/1995 | Taylor et al. |
| 5,598,453 | A | 1/1997 | Baba et al. |
| 5,772,594 | A | 6/1998 | Barrick |
| 5,791,908 | A | 8/1998 | Gillio |
| 5,820,559 | A | 10/1998 | Ng et al. |

(Continued)

OTHER PUBLICATIONS

US 8,231,638 B2, 07/2012, Swarup et al. (withdrawn)

*Primary Examiner* — Joseph M Dietrich

(57) ABSTRACT

A medical implant includes an implant component configured to be implanted in a patient, an electrode array, an energy storage device, a wireless communication interface, and implant circuitry. The electrode array includes sensor electrodes spaced apart on the implant component. The energy storage device, wireless communication interface, and implant circuitry are inside the implant component. The wireless communication interface is configured to communicate with a wireless receiver that is separate from the medical implant. The implant circuitry is operative to supply voltage to at least one of the sensor electrodes to measure electrical and/or chemical characteristics associated with when a biofilm is forming on the implant component, and communicate signaling indicating the electrical and/or chemical characteristics through the wireless communication interface.

18 Claims, 20 Drawing Sheets

(56) References Cited

U.S. PATENT DOCUMENTS 5,825,982 A 10/1998 Wright et al.
5,887,121 A 3/1999 Funda et al.
5,911,449 A 6/1999 Daniele et al.
5,951,475 A 9/1999 Gueziec et al.
5,987,960 A 11/1999 Messner et al.
6,012,216 A 1/2000 Esteves et al.
6,031,888 A 2/2000 Ivan et al.
6,033,415 A 3/2000 Mittelstadt et al.
6,080,181 A 6/2000 Jensen et al.
6,106,511 A 8/2000 Jensen
6,122,541 A 9/2000 Cosman et al.
6,144,875 A 11/2000 Schweikard et al.
6,157,853 A 12/2000 Blume et al.
6,167,145 A 12/2000 Foley et al.
6,167,292 A 12/2000 Badano et al.
6,201,984 B1 3/2001 Funda et al.
6,203,196 B1 3/2001 Meyer et al.
6,205,411 B1 3/2001 DiGioia, III et al.
6,212,419 B1 4/2001 Blume et al.
6,231,565 B1 5/2001 Tovey et al.
6,236,875 B1 5/2001 Bucholz et al.
6,246,900 B1 6/2001 Cosman et al.
6,301,495 B1 10/2001 Gueziec et al.
6,306,126 B1 10/2001 Montezuma
6,312,435 B1 11/2001 Wallace et al.
6,314,311 B1 11/2001 Williams et al.
6,320,929 B1 11/2001 Von Der Haar
6,322,567 B1 11/2001 Mittelstadt et al.
6,325,808 B1 12/2001 Bernard et al.
6,340,363 B1 1/2002 Bolger et al.
6,377,011 B1 4/2002 Ben-Ur
6,379,302 B1 4/2002 Kessman et al.
6,402,762 B2 6/2002 Hunter et al.
6,424,885 B1 7/2002 Niemeyer et al.
6,447,503 B1 9/2002 Wynne et al.
6,451,027 B1 9/2002 Cooper et al.
6,477,400 B1 11/2002 Barrick
6,484,049 B1 11/2002 Seeley et al.
6,487,267 B1 11/2002 Wolter
6,490,467 B1 12/2002 Bucholz et al.
6,490,475 B1 12/2002 Seeley et al.
6,499,488 B1 12/2002 Hunter et al.
6,501,981 B1 12/2002 Schweikard et al.
6,507,751 B2 1/2003 Blume et al.
6,535,756 B1 3/2003 Simon et al.
6,560,354 B1 5/2003 Maurer, Jr. et al.
6,565,554 B1 5/2003 Niemeyer
6,587,750 B2 7/2003 Gerbi et al.
6,614,453 B1 9/2003 Suri et al.
6,614,871 B1 9/2003 Kobiki et al.
6,619,840 B2 9/2003 Rasche et al.
6,636,757 B1 10/2003 Jascob et al.
6,645,196 B1 11/2003 Nixon et al.
6,666,579 B2 12/2003 Jensen
6,669,635 B2 12/2003 Kessman et al.
6,701,173 B2 3/2004 Nowinski et al.
6,757,068 B2 6/2004 Foxlin
6,782,287 B2 8/2004 Grzeszczuk et al.
6,783,524 B2 8/2004 Anderson et al.
6,786,896 B1 9/2004 Madhani et al.
6,788,018 B1 9/2004 Blumenkranz
6,804,581 B2 10/2004 Wang et al.
6,823,207 B1 11/2004 Jensen et al.
6,827,351 B2 12/2004 Graziani et al.
6,837,892 B2 1/2005 Shoham
6,839,612 B2 1/2005 Sanchez et al.
6,856,826 B2 2/2005 Seeley et al.
6,856,827 B2 2/2005 Seeley et al.
6,879,880 B2 4/2005 Nowlin et al.
6,892,090 B2 5/2005 Verard et al.
6,920,347 B2 7/2005 Simon et al.
6,922,632 B2 7/2005 Foxlin
6,968,224 B2 11/2005 Kessman et al.
6,978,166 B2 12/2005 Foley et al.
6,988,009 B2 1/2006 Grimm et al.
6,991,627 B2 1/2006 Madhani et al.
6,996,487 B2 2/2006 Jutras et al.
6,999,852 B2 2/2006 Green
7,007,699 B2 3/2006 Martinelli et al.
7,016,457 B1 3/2006 Senzig et al.
7,043,961 B2 5/2006 Pandey et al.
7,062,006 B1 6/2006 Pelc et al.
7,063,705 B2 6/2006 Young et al.
7,072,707 B2 7/2006 Galloway, Jr. et al.
7,083,615 B2 8/2006 Peterson et al.
7,097,640 B2 8/2006 Wang et al.
7,099,428 B2 8/2006 Clinthorne et al.
7,108,421 B2 9/2006 Gregerson et al.
7,130,676 B2 10/2006 Barrick
7,139,418 B2 11/2006 Abovitz et al.
7,139,601 B2 11/2006 Bucholz et al.
7,155,316 B2 12/2006 Sutherland et al.
7,164,968 B2 1/2007 Treat et al.
7,167,738 B2 1/2007 Schweikard et al.
7,169,141 B2 1/2007 Brock et al.
7,172,627 B2 2/2007 Fiere et al.
7,194,120 B2 3/2007 Wicker et al.
7,197,107 B2 3/2007 Arai et al.
7,231,014 B2 6/2007 Levy
7,231,063 B2 6/2007 Naimark et al.
7,239,940 B2 7/2007 Wang et al.
7,248,914 B2 7/2007 Hastings et al.
7,301,648 B2 11/2007 Foxlin
7,302,288 B1 11/2007 Schellenberg
7,313,430 B2 12/2007 Urquhart et al.
7,318,805 B2 1/2008 Schweikard et al.
7,318,827 B2 1/2008 Leitner et al.
7,319,897 B2 1/2008 Leitner et al.
7,324,623 B2 1/2008 Heuscher et al.
7,327,865 B2 2/2008 Fu et al.
7,331,967 B2 2/2008 Lee et al.
7,333,642 B2 2/2008 Green
7,339,341 B2 3/2008 Oleynikov et al.
7,366,562 B2 4/2008 Dukesherer et al.
7,379,790 B2 5/2008 Toth et al.
7,386,365 B2 6/2008 Nixon
7,422,592 B2 9/2008 Morley et al.
7,435,216 B2 10/2008 Kwon et al.
7,440,793 B2 10/2008 Chauhan et al.
7,460,637 B2 12/2008 Clinthorne et al.
7,466,303 B2 12/2008 Yi et al.
7,493,153 B2 2/2009 Ahmed et al.
7,505,617 B2 3/2009 Fu et al.
7,533,892 B2 5/2009 Schena et al.
7,542,791 B2 6/2009 Mire et al.
7,555,331 B2 6/2009 Viswanathan
7,567,834 B2 7/2009 Clayton et al.
7,594,912 B2 9/2009 Cooper et al.
7,606,613 B2 10/2009 Simon et al.
7,607,440 B2 10/2009 Coste-Maniere et al.
7,623,902 B2 11/2009 Pacheco
7,630,752 B2 12/2009 Viswanathan
7,630,753 B2 12/2009 Simon et al.
7,643,862 B2 1/2010 Schoenefeld
7,660,623 B2 2/2010 Hunter et al.
7,661,881 B2 2/2010 Gregerson et al.
7,683,331 B2 3/2010 Chang
7,683,332 B2 3/2010 Chang
7,689,320 B2 3/2010 Prisco et al.
7,691,098 B2 4/2010 Wallace et al.
7,702,379 B2 4/2010 Avinash et al.
7,702,477 B2 4/2010 Tuemmler et al.
7,711,083 B2 5/2010 Heigl et al.
7,711,406 B2 5/2010 Kuhn et al.
7,720,523 B2 5/2010 Omernick et al.
7,725,253 B2 5/2010 Foxlin
7,726,171 B2 6/2010 Langlotz et al.
7,742,801 B2 6/2010 Neubauer et al.
7,751,865 B2 7/2010 Jascob et al.
7,760,849 B2 7/2010 Zhang
7,762,825 B2 7/2010 Burbank et al.
7,763,015 B2 7/2010 Cooper et al.
7,787,699 B2 8/2010 Mahesh et al.
7,796,728 B2 9/2010 Bergfjord

(56) References Cited

U.S. PATENT DOCUMENTS

| | | | |
|---|---|---|---|
| 7,813,838 | B2 | 10/2010 | Sommer |
| 7,818,044 | B2 | 10/2010 | Dukesherer et al. |
| 7,819,859 | B2 | 10/2010 | Prisco et al. |
| 7,824,401 | B2 | 11/2010 | Manzo et al. |
| 7,831,294 | B2 | 11/2010 | Viswanathan |
| 7,834,484 | B2 | 11/2010 | Sartor |
| 7,835,557 | B2 | 11/2010 | Kendrick et al. |
| 7,835,778 | B2 | 11/2010 | Foley et al. |
| 7,835,784 | B2 | 11/2010 | Mire et al. |
| 7,840,253 | B2 | 11/2010 | Tremblay et al. |
| 7,840,256 | B2 | 11/2010 | Lakin et al. |
| 7,843,158 | B2 | 11/2010 | Prisco |
| 7,844,320 | B2 | 11/2010 | Shahidi |
| 7,853,305 | B2 | 12/2010 | Simon et al. |
| 7,853,313 | B2 | 12/2010 | Thompson |
| 7,865,269 | B2 | 1/2011 | Prisco et al. |
| D631,966 | S | 2/2011 | Perloff et al. |
| 7,879,045 | B2 | 2/2011 | Gielen et al. |
| 7,881,767 | B2 | 2/2011 | Strommer et al. |
| 7,881,770 | B2 | 2/2011 | Melkent et al. |
| 7,886,743 | B2 | 2/2011 | Cooper et al. |
| RE42,194 | E | 3/2011 | Foley et al. |
| RE42,226 | E | 3/2011 | Foley et al. |
| 7,900,524 | B2 | 3/2011 | Calloway et al. |
| 7,907,166 | B2 | 3/2011 | Lamprecht et al. |
| 7,909,122 | B2 | 3/2011 | Schena et al. |
| 7,925,653 | B2 | 4/2011 | Saptharishi |
| 7,930,065 | B2 | 4/2011 | Larkin et al. |
| 7,935,130 | B2 | 5/2011 | Willliams |
| 7,940,999 | B2 | 5/2011 | Liao et al. |
| 7,945,012 | B2 | 5/2011 | Ye et al. |
| 7,945,021 | B2 | 5/2011 | Shapiro et al. |
| 7,953,470 | B2 | 5/2011 | Vetter et al. |
| 7,954,397 | B2 | 6/2011 | Choi et al. |
| 7,971,341 | B2 | 7/2011 | Dukesherer et al. |
| 7,974,674 | B2 | 7/2011 | Hauck et al. |
| 7,974,677 | B2 | 7/2011 | Mire et al. |
| 7,974,681 | B2 | 7/2011 | Wallace et al. |
| 7,979,157 | B2 | 7/2011 | Anvari |
| 7,983,733 | B2 | 7/2011 | Viswanathan |
| 7,988,215 | B2 | 8/2011 | Seibold |
| 7,996,110 | B2 | 8/2011 | Lipow et al. |
| 8,004,121 | B2 | 8/2011 | Sartor |
| 8,004,229 | B2 | 8/2011 | Nowlin et al. |
| 8,010,177 | B2 | 8/2011 | Csavoy et al. |
| 8,019,045 | B2 | 9/2011 | Kato |
| 8,021,310 | B2 | 9/2011 | Sanborn et al. |
| 8,035,685 | B2 | 10/2011 | Jensen |
| 8,046,054 | B2 | 10/2011 | Kim et al. |
| 8,046,057 | B2 | 10/2011 | Clarke |
| 8,052,688 | B2 | 11/2011 | Wolf, II |
| 8,054,184 | B2 | 11/2011 | Cline et al. |
| 8,054,752 | B2 | 11/2011 | Druke et al. |
| 8,057,397 | B2 | 11/2011 | Li et al. |
| 8,057,407 | B2 | 11/2011 | Martinelli et al. |
| 8,062,288 | B2 | 11/2011 | Cooper et al. |
| 8,062,375 | B2 | 11/2011 | Glerum et al. |
| 8,066,524 | B2 | 11/2011 | Burbank et al. |
| 8,073,335 | B2 | 12/2011 | Labonville et al. |
| 8,079,950 | B2 | 12/2011 | Stern et al. |
| 8,086,299 | B2 | 12/2011 | Adler et al. |
| 8,092,370 | B2 | 1/2012 | Roberts et al. |
| 8,098,914 | B2 | 1/2012 | Liao et al. |
| 8,100,950 | B2 | 1/2012 | St. Clair et al. |
| 8,105,320 | B2 | 1/2012 | Manzo |
| 8,108,025 | B2 | 1/2012 | Csavoy et al. |
| 8,109,877 | B2 | 2/2012 | Moctezuma de la Barrera et al. |
| 8,112,292 | B2 | 2/2012 | Simon |
| 8,116,430 | B1 | 2/2012 | Shapiro et al. |
| 8,120,301 | B2 | 2/2012 | Goldberg et al. |
| 8,121,249 | B2 | 2/2012 | Wang et al. |
| 8,123,675 | B2 | 2/2012 | Funda et al. |
| 8,133,229 | B1 | 3/2012 | Bonutti |
| 8,142,420 | B2 | 3/2012 | Schena |
| 8,147,494 | B2 | 4/2012 | Leitner et al. |
| 8,150,494 | B2 | 4/2012 | Simon et al. |
| 8,150,497 | B2 | 4/2012 | Gielen et al. |
| 8,150,498 | B2 | 4/2012 | Gielen et al. |
| 8,165,658 | B2 | 4/2012 | Waynik et al. |
| 8,170,313 | B2 | 5/2012 | Kendrick et al. |
| 8,179,073 | B2 | 5/2012 | Farritor et al. |
| 8,182,476 | B2 | 5/2012 | Julian et al. |
| 8,184,880 | B2 | 5/2012 | Zhao et al. |
| 8,202,278 | B2 | 6/2012 | Orban, III et al. |
| 8,208,708 | B2 | 6/2012 | Homan et al. |
| 8,208,988 | B2 | 6/2012 | Jensen |
| 8,219,177 | B2 | 7/2012 | Smith et al. |
| 8,219,178 | B2 | 7/2012 | Smith et al. |
| 8,220,468 | B2 | 7/2012 | Cooper et al. |
| 8,224,024 | B2 | 7/2012 | Foxlin et al. |
| 8,224,484 | B2 | 7/2012 | Swarup et al. |
| 8,225,798 | B2 | 7/2012 | Baldwin et al. |
| 8,228,368 | B2 | 7/2012 | Zhao et al. |
| 8,231,610 | B2 | 7/2012 | Jo et al. |
| 8,239,001 | B2 | 8/2012 | Verard et al. |
| 8,241,271 | B2 | 8/2012 | Millman et al. |
| 8,248,413 | B2 | 8/2012 | Gattani et al. |
| 8,256,319 | B2 | 9/2012 | Cooper et al. |
| 8,263,933 | B2 | 9/2012 | Zeile |
| 8,271,069 | B2 | 9/2012 | Jascob et al. |
| 8,271,130 | B2 | 9/2012 | Hourtash |
| 8,281,670 | B2 | 10/2012 | Larkin et al. |
| 8,282,653 | B2 | 10/2012 | Nelson et al. |
| 8,301,226 | B2 | 10/2012 | Csavoy et al. |
| 8,311,611 | B2 | 11/2012 | Csavoy et al. |
| 8,320,991 | B2 | 11/2012 | Jascob et al. |
| 8,332,012 | B2 | 12/2012 | Kienzle, III |
| 8,333,755 | B2 | 12/2012 | Cooper et al. |
| 8,335,552 | B2 | 12/2012 | Stiles |
| 8,335,557 | B2 | 12/2012 | Maschke |
| 8,348,931 | B2 | 1/2013 | Cooper et al. |
| 8,353,963 | B2 | 1/2013 | Glerum |
| 8,358,818 | B2 | 1/2013 | Miga et al. |
| 8,359,730 | B2 | 1/2013 | Burg et al. |
| 8,374,673 | B2 | 2/2013 | Adcox et al. |
| 8,374,723 | B2 | 2/2013 | Zhao et al. |
| 8,379,791 | B2 | 2/2013 | Forthmann et al. |
| 8,386,019 | B2 | 2/2013 | Camus et al. |
| 8,392,022 | B2 | 3/2013 | Ortmaier et al. |
| 8,394,099 | B2 | 3/2013 | Patwardhan |
| 8,395,342 | B2 | 3/2013 | Prisco |
| 8,398,634 | B2 | 3/2013 | Manzo et al. |
| 8,400,094 | B2 | 3/2013 | Schena |
| 8,414,957 | B2 | 4/2013 | Enzerink et al. |
| 8,418,073 | B2 | 4/2013 | Mohr et al. |
| 8,450,694 | B2 | 5/2013 | Baviera et al. |
| 8,452,447 | B2 | 5/2013 | Nixon |
| RE44,305 | E | 6/2013 | Foley et al. |
| 8,462,911 | B2 | 6/2013 | Vesel et al. |
| 8,465,476 | B2 | 6/2013 | Rogers et al. |
| 8,465,771 | B2 | 6/2013 | Wan et al. |
| 8,467,851 | B2 | 6/2013 | Mire et al. |
| 8,467,852 | B2 | 6/2013 | Csavoy et al. |
| 8,469,947 | B2 | 6/2013 | Devengenzo et al. |
| RE44,392 | E | 7/2013 | Hynes |
| 8,483,434 | B2 | 7/2013 | Buehner et al. |
| 8,483,800 | B2 | 7/2013 | Jensen et al. |
| 8,486,532 | B2 | 7/2013 | Enzerink et al. |
| 8,489,235 | B2 | 7/2013 | Moll et al. |
| 8,500,722 | B2 | 8/2013 | Cooper |
| 8,500,728 | B2 | 8/2013 | Newton et al. |
| 8,504,201 | B2 | 8/2013 | Moll et al. |
| 8,506,555 | B2 | 8/2013 | Ruiz Morales |
| 8,506,556 | B2 | 8/2013 | Schena |
| 8,508,173 | B2 | 8/2013 | Goldberg et al. |
| 8,512,318 | B2 | 8/2013 | Tovey et al. |
| 8,515,576 | B2 | 8/2013 | Lipow et al. |
| 8,518,120 | B2 | 8/2013 | Glerum et al. |
| 8,521,331 | B2 | 8/2013 | Itkowitz |
| 8,526,688 | B2 | 9/2013 | Groszmann et al. |
| 8,526,700 | B2 | 9/2013 | Isaacs |
| 8,527,094 | B2 | 9/2013 | Kumar et al. |
| 8,528,440 | B2 | 9/2013 | Morley et al. |
| 8,532,741 | B2 | 9/2013 | Heruth et al. |

(56) References Cited

U.S. PATENT DOCUMENTS

| | | | |
|---|---|---|---|
| 8,541,970 | B2 | 9/2013 | Nowlin et al. |
| 8,548,563 | B2 | 10/2013 | Simon et al. |
| 8,549,732 | B2 | 10/2013 | Burg et al. |
| 8,551,114 | B2 | 10/2013 | Ramos de la Pena |
| 8,551,116 | B2 | 10/2013 | Julian et al. |
| 8,556,807 | B2 | 10/2013 | Scott et al. |
| 8,556,979 | B2 | 10/2013 | Glerum et al. |
| 8,560,118 | B2 | 10/2013 | Green et al. |
| 8,561,473 | B2 | 10/2013 | Blumenkranz |
| 8,562,594 | B2 | 10/2013 | Cooper et al. |
| 8,571,638 | B2 | 10/2013 | Shoham |
| 8,571,710 | B2 | 10/2013 | Coste-Maniere et al. |
| 8,573,465 | B2 | 11/2013 | Shelton, IV |
| 8,574,303 | B2 | 11/2013 | Sharkey et al. |
| 8,585,420 | B2 | 11/2013 | Burbank et al. |
| 8,594,841 | B2 | 11/2013 | Zhao et al. |
| 8,597,198 | B2 | 12/2013 | Sanborn et al. |
| 8,600,478 | B2 | 12/2013 | Verard et al. |
| 8,603,077 | B2 | 12/2013 | Cooper et al. |
| 8,611,985 | B2 | 12/2013 | Lavallee et al. |
| 8,613,230 | B2 | 12/2013 | Blumenkranz et al. |
| 8,621,939 | B2 | 1/2014 | Blumenkranz et al. |
| 8,624,537 | B2 | 1/2014 | Nowlin et al. |
| 8,630,389 | B2 | 1/2014 | Kato |
| 8,634,897 | B2 | 1/2014 | Simon et al. |
| 8,634,957 | B2 | 1/2014 | Toth et al. |
| 8,638,056 | B2 | 1/2014 | Goldberg et al. |
| 8,638,057 | B2 | 1/2014 | Goldberg et al. |
| 8,639,000 | B2 | 1/2014 | Zhao et al. |
| 8,641,726 | B2 | 2/2014 | Bonutti |
| 8,644,907 | B2 | 2/2014 | Hartmann et al. |
| 8,657,809 | B2 | 2/2014 | Schoepp |
| 8,660,635 | B2 | 2/2014 | Simon et al. |
| 8,666,544 | B2 | 3/2014 | Moll et al. |
| 8,675,939 | B2 | 3/2014 | Moctezuma de la Barrera |
| 8,678,647 | B2 | 3/2014 | Gregerson et al. |
| 8,679,125 | B2 | 3/2014 | Smith et al. |
| 8,679,183 | B2 | 3/2014 | Glerum et al. |
| 8,682,413 | B2 | 3/2014 | Lloyd |
| 8,684,253 | B2 | 4/2014 | Giordano et al. |
| 8,685,098 | B2 | 4/2014 | Glerum et al. |
| 8,693,730 | B2 | 4/2014 | Umasuthan et al. |
| 8,694,075 | B2 | 4/2014 | Groszmann et al. |
| 8,696,458 | B2 | 4/2014 | Foxlin et al. |
| 8,700,123 | B2 | 4/2014 | Okamura et al. |
| 8,706,086 | B2 | 4/2014 | Glerum |
| 8,706,185 | B2 | 4/2014 | Foley et al. |
| 8,706,301 | B2 | 4/2014 | Zhao et al. |
| 8,717,430 | B2 | 5/2014 | Simon et al. |
| 8,727,618 | B2 | 5/2014 | Maschke et al. |
| 8,734,432 | B2 | 5/2014 | Tuma et al. |
| 8,738,115 | B2 | 5/2014 | Amberg et al. |
| 8,738,181 | B2 | 5/2014 | Greer et al. |
| 8,740,882 | B2 | 6/2014 | Jun et al. |
| 8,746,252 | B2 | 6/2014 | McGrogan et al. |
| 8,749,189 | B2 | 6/2014 | Nowlin et al. |
| 8,749,190 | B2 | 6/2014 | Nowlin et al. |
| 8,761,930 | B2 | 6/2014 | Nixon |
| 8,764,448 | B2 | 7/2014 | Yang et al. |
| 8,771,170 | B2 | 7/2014 | Mesallum et al. |
| 8,781,186 | B2 | 7/2014 | Clements et al. |
| 8,781,630 | B2 | 7/2014 | Banks et al. |
| 8,784,385 | B2 | 7/2014 | Boyden et al. |
| 8,786,241 | B2 | 7/2014 | Nowlin et al. |
| 8,787,520 | B2 | 7/2014 | Baba |
| 8,792,704 | B2 | 7/2014 | Isaacs |
| 8,798,231 | B2 | 8/2014 | Notohara et al. |
| 8,800,838 | B2 | 8/2014 | Shelton, IV |
| 8,808,164 | B2 | 8/2014 | Hoffman et al. |
| 8,812,077 | B2 | 8/2014 | Dempsey |
| 8,814,793 | B2 | 8/2014 | Brabrand |
| 8,816,628 | B2 | 8/2014 | Nowlin et al. |
| 8,818,105 | B2 | 8/2014 | Myronenko et al. |
| 8,820,605 | B2 | 9/2014 | Shelton, IV |
| 8,821,511 | B2 | 9/2014 | Von Jako et al. |
| 8,823,308 | B2 | 9/2014 | Nowlin et al. |
| 8,827,996 | B2 | 9/2014 | Scott et al. |
| 8,828,024 | B2 | 9/2014 | Farritor et al. |
| 8,830,224 | B2 | 9/2014 | Zhao et al. |
| 8,834,489 | B2 | 9/2014 | Cooper et al. |
| 8,834,490 | B2 | 9/2014 | Bonutti |
| 8,838,270 | B2 | 9/2014 | Druke et al. |
| 8,844,789 | B2 | 9/2014 | Shelton, IV et al. |
| 8,855,822 | B2 | 10/2014 | Bartol et al. |
| 8,858,598 | B2 | 10/2014 | Seifert et al. |
| 8,860,753 | B2 | 10/2014 | Bhandarkar et al. |
| 8,864,751 | B2 | 10/2014 | Prisco et al. |
| 8,864,798 | B2 | 10/2014 | Weiman et al. |
| 8,864,833 | B2 | 10/2014 | Glerum et al. |
| 8,867,703 | B2 | 10/2014 | Shapiro et al. |
| 8,870,880 | B2 | 10/2014 | Himmelberger et al. |
| 8,876,866 | B2 | 11/2014 | Zappacosta et al. |
| 8,880,223 | B2 | 11/2014 | Raj et al. |
| 8,882,803 | B2 | 11/2014 | Iott et al. |
| 8,883,210 | B1 | 11/2014 | Truncale et al. |
| 8,888,821 | B2 | 11/2014 | Rezach et al. |
| 8,888,853 | B2 | 11/2014 | Glerum et al. |
| 8,888,854 | B2 | 11/2014 | Glerum et al. |
| 8,894,652 | B2 | 11/2014 | Seifert et al. |
| 8,894,688 | B2 | 11/2014 | Suh |
| 8,894,691 | B2 | 11/2014 | Iott et al. |
| 8,906,069 | B2 | 12/2014 | Hansell et al. |
| 8,964,934 | B2 | 2/2015 | Ein-Gal |
| 8,992,580 | B2 | 3/2015 | Bar et al. |
| 8,996,169 | B2 | 3/2015 | Lightcap et al. |
| 9,001,963 | B2 | 4/2015 | Sowards-Emmerd et al. |
| 9,002,076 | B2 | 4/2015 | Khadem et al. |
| 9,044,190 | B2 | 6/2015 | Rubner et al. |
| 9,107,683 | B2 | 8/2015 | Hourtash et al. |
| 9,125,556 | B2 | 9/2015 | Zehavi et al. |
| 9,131,986 | B2 | 9/2015 | Greer et al. |
| 9,215,968 | B2 | 12/2015 | Schostek et al. |
| 9,308,050 | B2 | 4/2016 | Kostrzewski et al. |
| 9,380,984 | B2 | 7/2016 | Li et al. |
| 9,393,039 | B2 | 7/2016 | Lechner et al. |
| 9,398,886 | B2 | 7/2016 | Gregerson et al. |
| 9,398,890 | B2 | 7/2016 | Dong et al. |
| 9,414,859 | B2 | 8/2016 | Ballard et al. |
| 9,420,975 | B2 | 8/2016 | Gutfleisch et al. |
| 9,492,235 | B2 | 11/2016 | Hourtash et al. |
| 9,592,096 | B2 | 3/2017 | Maillet et al. |
| 9,750,465 | B2 | 9/2017 | Engel et al. |
| 9,757,203 | B2 | 9/2017 | Hourtash et al. |
| 9,795,354 | B2 | 10/2017 | Menegaz et al. |
| 9,814,535 | B2 | 11/2017 | Bar et al. |
| 9,820,783 | B2 | 11/2017 | Donner et al. |
| 9,833,265 | B2 | 12/2017 | Donner et al. |
| 9,848,922 | B2 | 12/2017 | Tohmeh et al. |
| 9,925,011 | B2 | 3/2018 | Gombert et al. |
| 9,931,025 | B1 | 4/2018 | Graetzel et al. |
| 10,034,717 | B2 | 7/2018 | Miller et al. |
| 2001/0036302 | A1 | 11/2001 | Miller |
| 2002/0035321 | A1 | 3/2002 | Bucholz et al. |
| 2004/0068172 | A1 | 4/2004 | Nowinski et al. |
| 2004/0076259 | A1 | 4/2004 | Jensen et al. |
| 2005/0096502 | A1 | 5/2005 | Khalili |
| 2005/0143651 | A1 | 6/2005 | Verard et al. |
| 2005/0171558 | A1 | 8/2005 | Abovitz et al. |
| 2006/0100610 | A1 | 5/2006 | Wallace et al. |
| 2006/0173329 | A1 | 8/2006 | Marquart et al. |
| 2006/0184396 | A1 | 8/2006 | Dennis et al. |
| 2006/0241416 | A1 | 10/2006 | Marquart et al. |
| 2006/0291612 | A1 | 12/2006 | Nishide et al. |
| 2007/0015987 | A1 | 1/2007 | Benlloch Baviera et al. |
| 2007/0021738 | A1 | 1/2007 | Hasser et al. |
| 2007/0038059 | A1 | 2/2007 | Sheffer et al. |
| 2007/0073133 | A1 | 3/2007 | Schoenefeld |
| 2007/0156121 | A1 | 7/2007 | Millman et al. |
| 2007/0156157 | A1 | 7/2007 | Nahum et al. |
| 2007/0167712 | A1 | 7/2007 | Keglovich et al. |
| 2007/0233238 | A1 | 10/2007 | Huynh et al. |
| 2008/0004523 | A1 | 1/2008 | Jensen |
| 2008/0013809 | A1 | 1/2008 | Zhu et al. |
| 2008/0033283 | A1 | 2/2008 | Dellaca et al. |

(56) References Cited

U.S. PATENT DOCUMENTS

2008/0046122 A1 2/2008 Manzo et al.
2008/0082109 A1 4/2008 Moll et al.
2008/0108912 A1 5/2008 Node-Langlois
2008/0108991 A1 5/2008 Von Jako
2008/0109012 A1 5/2008 Falco et al.
2008/0144906 A1 6/2008 Allred et al.
2008/0161680 A1 7/2008 Von Jako et al.
2008/0161682 A1 7/2008 Kendrick et al.
2008/0177203 A1 7/2008 von Jako
2008/0214922 A1 9/2008 Hartmann et al.
2008/0228068 A1 9/2008 Viswanathan et al.
2008/0228196 A1 9/2008 Wang et al.
2008/0235052 A1 9/2008 Node-Langlois et al.
2008/0269596 A1 10/2008 Revie et al.
2008/0287771 A1 11/2008 Anderson
2008/0287781 A1 11/2008 Revie et al.
2008/0300477 A1 12/2008 Lloyd et al.
2008/0300478 A1 12/2008 Zuhars et al.
2008/0302950 A1 12/2008 Park et al.
2008/0306490 A1 12/2008 Lakin et al.
2008/0319311 A1 12/2008 Hamadeh
2009/0012509 A1 1/2009 Csavoy et al.
2009/0030428 A1 1/2009 Omori et al.
2009/0080737 A1 3/2009 Battle et al.
2009/0185655 A1 7/2009 Koken et al.
2009/0198121 A1 8/2009 Hoheisel
2009/0216113 A1 8/2009 Meier et al.
2009/0228019 A1 9/2009 Gross et al.
2009/0259123 A1 10/2009 Navab et al.
2009/0259230 A1 10/2009 Khadem et al.
2009/0264899 A1 10/2009 Appenrodt et al.
2009/0281417 A1 11/2009 Hartmann et al.
2010/0022874 A1 1/2010 Wang et al.
2010/0039506 A1 2/2010 Sarvestani et al.
2010/0125286 A1 5/2010 Wang et al.
2010/0130986 A1 5/2010 Mailloux et al.
2010/0228117 A1 9/2010 Hartmann
2010/0228265 A1 9/2010 Prisco
2010/0249571 A1 9/2010 Jensen et al.
2010/0274120 A1 10/2010 Heuscher
2010/0280363 A1 11/2010 Skarda et al.
2010/0331858 A1 12/2010 Simaan et al.
2011/0022229 A1 1/2011 Jang et al.
2011/0077504 A1 3/2011 Fischer et al.
2011/0098553 A1 4/2011 Robbins et al.
2011/0137152 A1 6/2011 Li
2011/0213384 A1 9/2011 Jeong
2011/0224684 A1 9/2011 Larkin et al.
2011/0224685 A1 9/2011 Larkin et al.
2011/0224686 A1 9/2011 Larkin et al.
2011/0224687 A1 9/2011 Larkin et al.
2011/0224688 A1 9/2011 Larkin et al.
2011/0224689 A1 9/2011 Larkin et al.
2011/0224825 A1 9/2011 Larkin et al.
2011/0230967 A1 9/2011 O'Halloran et al.
2011/0238080 A1 9/2011 Ranjit et al.
2011/0276058 A1 11/2011 Choi et al.
2011/0282189 A1 11/2011 Graumann
2011/0286573 A1 11/2011 Schretter et al.
2011/0295062 A1 12/2011 Solsona et al.
2011/0295370 A1 12/2011 Suh et al.
2011/0306986 A1 12/2011 Lee et al.
2012/0035507 A1 2/2012 George et al.
2012/0046668 A1 2/2012 Gantes
2012/0051498 A1 3/2012 Koishi
2012/0053597 A1 3/2012 Anvari et al.
2012/0059248 A1 3/2012 Holsing et al.
2012/0071753 A1 3/2012 Hunter et al.
2012/0108954 A1 5/2012 Schulhauser et al.
2012/0136372 A1 5/2012 Amat Girbau et al.
2012/0143084 A1 6/2012 Shoham
2012/0184839 A1 7/2012 Woerlein
2012/0197182 A1 8/2012 Millman et al.
2012/0226145 A1 9/2012 Chang et al.
2012/0235909 A1 9/2012 Birkenbach et al.
2012/0245596 A1 9/2012 Meenink
2012/0253332 A1 10/2012 Moll
2012/0253360 A1 10/2012 White et al.
2012/0256092 A1 10/2012 Zingerman
2012/0294498 A1 11/2012 Popovic
2012/0296203 A1 11/2012 Hartmann et al.
2013/0006267 A1 1/2013 Odermatt et al.
2013/0016889 A1 1/2013 Myronenko et al.
2013/0030571 A1 1/2013 Ruiz Morales et al.
2013/0035583 A1 2/2013 Park et al.
2013/0060146 A1 3/2013 Yang et al.
2013/0060337 A1 3/2013 Petersheim et al.
2013/0094742 A1 4/2013 Feilkas
2013/0096574 A1 4/2013 Kang et al.
2013/0113791 A1 5/2013 Isaacs et al.
2013/0116706 A1 5/2013 Lee et al.
2013/0131695 A1 5/2013 Scarfogliero et al.
2013/0144307 A1 6/2013 Jeong et al.
2013/0158542 A1 6/2013 Manzo et al.
2013/0165937 A1 6/2013 Patwardhan
2013/0178867 A1 7/2013 Farritor et al.
2013/0178868 A1 7/2013 Roh
2013/0178870 A1 7/2013 Schena
2013/0204271 A1 8/2013 Brisson et al.
2013/0211419 A1 8/2013 Jensen
2013/0211420 A1 8/2013 Jensen
2013/0218142 A1 8/2013 Tuma et al.
2013/0223702 A1 8/2013 Holsing et al.
2013/0225942 A1 8/2013 Holsing et al.
2013/0225943 A1 8/2013 Holsing et al.
2013/0231556 A1 9/2013 Holsing et al.
2013/0237995 A1 9/2013 Lee et al.
2013/0245375 A1 9/2013 DiMaio et al.
2013/0261640 A1 10/2013 Kim et al.
2013/0272488 A1 10/2013 Bailey et al.
2013/0272489 A1 10/2013 Dickman et al.
2013/0274761 A1 10/2013 Devengenzo et al.
2013/0281821 A1 10/2013 Liu et al.
2013/0296884 A1 11/2013 Taylor et al.
2013/0303887 A1 11/2013 Holsing et al.
2013/0307955 A1 11/2013 Deitz et al.
2013/0317521 A1 11/2013 Choi et al.
2013/0325033 A1 12/2013 Schena et al.
2013/0325035 A1 12/2013 Hauck et al.
2013/0331686 A1 12/2013 Freysinger et al.
2013/0331858 A1 12/2013 Devengenzo et al.
2013/0331861 A1 12/2013 Yoon
2013/0342578 A1 12/2013 Isaacs
2013/0345717 A1 12/2013 Markvicka et al.
2013/0345757 A1 12/2013 Stad
2014/0001235 A1 1/2014 Shelton, IV
2014/0012131 A1 1/2014 Heruth et al.
2014/0031664 A1 1/2014 Kang et al.
2014/0046128 A1 2/2014 Lee et al.
2014/0046132 A1 2/2014 Hoeg et al.
2014/0046340 A1 2/2014 Wilson et al.
2014/0049629 A1 2/2014 Siewerdsen et al.
2014/0058406 A1 2/2014 Tsekos
2014/0073914 A1 3/2014 Lavallee et al.
2014/0080086 A1 3/2014 Chen
2014/0081128 A1 3/2014 Verard et al.
2014/0088612 A1 3/2014 Bartol et al.
2014/0094694 A1 4/2014 Moctezuma de la Barrera
2014/0094851 A1 4/2014 Gordon
2014/0096369 A1 4/2014 Matsumoto et al.
2014/0100587 A1 4/2014 Farritor et al.
2014/0121676 A1 5/2014 Kostrzewski et al.
2014/0128882 A1 5/2014 Kwak et al.
2014/0130810 A1 5/2014 Azizian et al.
2014/0135796 A1 5/2014 Simon et al.
2014/0142591 A1 5/2014 Alvarez et al.
2014/0142592 A1 5/2014 Moon et al.
2014/0148692 A1 5/2014 Hartmann et al.
2014/0163581 A1 6/2014 Devengenzo et al.
2014/0171781 A1 6/2014 Stiles
2014/0171900 A1 6/2014 Stiles
2014/0171965 A1 6/2014 Loh et al.
2014/0180308 A1 6/2014 von Grunberg
2014/0180309 A1 6/2014 Seeber et al.

(56) References Cited

U.S. PATENT DOCUMENTS

| | | | |
|---|---|---|---|
| 2014/0187915 | A1 | 7/2014 | Yaroshenko et al. |
| 2014/0188132 | A1 | 7/2014 | Kang |
| 2014/0194699 | A1 | 7/2014 | Roh et al. |
| 2014/0221819 | A1 | 8/2014 | Sarment |
| 2014/0222023 | A1 | 8/2014 | Kim et al. |
| 2014/0228631 | A1 | 8/2014 | Kwak et al. |
| 2014/0234804 | A1 | 8/2014 | Huang et al. |
| 2014/0257328 | A1 | 9/2014 | Kim et al. |
| 2014/0257329 | A1 | 9/2014 | Jang et al. |
| 2014/0257330 | A1 | 9/2014 | Choi et al. |
| 2014/0275760 | A1 | 9/2014 | Lee et al. |
| 2014/0275985 | A1 | 9/2014 | Walker et al. |
| 2014/0276931 | A1 | 9/2014 | Parihar et al. |
| 2014/0276940 | A1 | 9/2014 | Seo |
| 2014/0276944 | A1 | 9/2014 | Farritor et al. |
| 2014/0288413 | A1 | 9/2014 | Hwang et al. |
| 2014/0299648 | A1 | 10/2014 | Shelton, IV et al. |
| 2014/0303434 | A1 | 10/2014 | Farritor et al. |
| 2014/0303643 | A1 | 10/2014 | Ha et al. |
| 2014/0305995 | A1 | 10/2014 | Shelton, IV et al. |
| 2014/0309659 | A1 | 10/2014 | Roh et al. |
| 2014/0316436 | A1 | 10/2014 | Bar et al. |
| 2014/0323803 | A1 | 10/2014 | Hoffman et al. |
| 2014/0324070 | A1 | 10/2014 | Min et al. |
| 2014/0330288 | A1 | 11/2014 | Date et al. |
| 2014/0364720 | A1 | 12/2014 | Darrow et al. |
| 2014/0371577 | A1 | 12/2014 | Maillet et al. |
| 2015/0039034 | A1 | 2/2015 | Frankel et al. |
| 2015/0085970 | A1 | 3/2015 | Bouhnik et al. |
| 2015/0146847 | A1 | 5/2015 | Liu |
| 2015/0150524 | A1 | 6/2015 | Yorkston et al. |
| 2015/0196261 | A1 | 7/2015 | Funk |
| 2015/0213633 | A1 | 7/2015 | Chang et al. |
| 2015/0335480 | A1 | 11/2015 | Alvarez et al. |
| 2015/0342647 | A1 | 12/2015 | Frankel et al. |
| 2016/0005194 | A1 | 1/2016 | Schretter et al. |
| 2016/0166329 | A1 | 6/2016 | Langan et al. |
| 2016/0235480 | A1 | 8/2016 | Scholl et al. |
| 2016/0249990 | A1 | 9/2016 | Glozman et al. |
| 2016/0302871 | A1 | 10/2016 | Gregerson et al. |
| 2016/0320322 | A1 | 11/2016 | Suzuki |
| 2016/0331335 | A1 | 11/2016 | Gregerson et al. |
| 2017/0135770 | A1 | 5/2017 | Scholl et al. |
| 2017/0143284 | A1 | 5/2017 | Sehnert et al. |
| 2017/0143426 | A1 | 5/2017 | Isaacs et al. |
| 2017/0156816 | A1 | 6/2017 | Ibrahim |
| 2017/0202629 | A1 | 7/2017 | Maillet et al. |
| 2017/0212723 | A1 | 7/2017 | Atarot et al. |
| 2017/0215825 | A1 | 8/2017 | Johnson et al. |
| 2017/0215826 | A1 | 8/2017 | Johnson et al. |
| 2017/0215827 | A1 | 8/2017 | Johnson et al. |
| 2017/0231710 | A1 | 8/2017 | Scholl et al. |
| 2017/0258426 | A1 | 9/2017 | Risher-Kelly et al. |
| 2017/0273748 | A1 | 9/2017 | Hourtash et al. |
| 2017/0296277 | A1 | 10/2017 | Hourtash et al. |
| 2017/0360493 | A1 | 12/2017 | Zucher et al. |
| 2019/0060556 | A1* | 2/2019 | Huiszoon .............. A61M 5/001 |

* cited by examiner

SMART IMPLANTS FOR PERIPROSTHETIC JOINT INFECTION

FIELD

The present disclosure relates to medical implants, such as for joint arthroplasty.

BACKGROUND

Periprosthetic joint infection (PJI) is one of the most feared complications in joint arthroplasty due to the ineffectiveness of antibiotics, invasive treatment options, and relatively high annual mortality rate of 4%. If caught early enough, antibiotics and natural immune responses are very effective at intercepting the free-floating bacteria within the surgical site. However, antibiotics are remarkably ineffective at eradicating bacteria within biofilm on the surface of the implant.

Biofilm develops as bacteria adhere to and colonize on the surface of an implant. The biofilm layer serves as a biochemical fortress that prevents penetration of antibiotic agents. It has been reported that 500-5000 times the concentration of antibiotics are required to have the same effectiveness on biofilm bacteria as compared to free-floating planktonic bacteria. As a result, the most common treatment for PJI is highly invasive two-stage revision.

Two-stage revision involves an initial operation to remove the septic implant and debride the surgical site and a second procedure to place new implant components. Although two-stage revision is the most common treatment option for PJI, the success rate has been reported to be only 85%. In addition, the risk of reinfection following revision for PJI has been reported to be 9% compared to 1-2% following the primary procedure. Also, the annual mortality rate has been reported to be as high as 14% following two-stage revision.

Much of the research and product development activity has been focused on preventing, rather than treating, infection following joint arthroplasty. Despite the incorporation of prevention strategies, including sterilization standards, shorter operative times, laminar airflow systems, body exhaust suits, perioperative antibiotics, antibiotic cement, and antimicrobial adhesive dressings, the incidence of PJI after THA and TKA has remained relatively constant over the past 20 years. This lack of improvement is likely due in part to the ineffectiveness of these solutions in preventing, detecting, and eradicating the pathogenesis of joint infection, which is the formation of biofilm.

SUMMARY

Embodiments of the present disclosure are directed to smart joint reconstruction implants that can provide physicians/clinicians and their patients the ability to monitor, detect, and diagnose PJI. These implants could also operate to detect and eradicate PJI, which may increase the effectiveness of antibiotics and reduce the prevalence of two-stage revision procedures.

Some embodiments of the present disclosure are directed to a medical implant that includes an implant component configured to be implanted in a patient, an electrode array with sensor electrodes spaced apart on the implant component, an energy storage device within the implant component, a wireless communication interface within the implant component, and implant circuitry within the implant component. The wireless communication interface is configured to communicate with a wireless receiver that is separate from the medical implant. The implant circuitry is operative to supply voltage to at least one of the sensor electrodes to measure electrical and/or chemical characteristics associated with when a biofilm is forming on the implant component, and communicate signaling indicating the electrical and/or chemical characteristics through the wireless communication interface.

Some other embodiments are directed to a corresponding computing device that includes a wireless communication interface and circuitry. The wireless communication interface is operative to receive, from a medical implant, signaling based on a measured electrical and/or chemical characteristics through sensor electrodes spaced apart on a component of the medical implant. The circuitry is operative to detect presence of a biofilm and a location of the biofilm on the medical implant based on the received signaling, and transmit a message that identifies stimulation electrodes, that are associated with the determined location of the biofilm, on the component of the medical implant that are to be stimulated by current supplied by implant circuitry at a level which reduces the biofilm.

Possible advantages that may be provided by one or one of these and other embodiments disclosed herein may include active prevention, early detection, and non-invasive eradiation of biofilm/bacteria. One or more of the embodiments may reduce the incidence of early postoperative infections by preventing development of biofilm and forcing the bacteria to remain free-floating, where it is vulnerable to natural immune responses and antibiotics. Additionally, the embodiment(s) may monitor the formation of biofilm to provide early detection of late chronic PJI and feedback on the effectiveness of treatment. The embodiment(s) may also provide a treatment option to increase the effectiveness of antibiotics and reduce the need for 2-stage revisions. If an infection is detected, either through the onset of symptoms or measured biofilm, an eradication modality can be utilized to directly kill adhered bacteria, detach the biofilm layer, and expel bacteria into the surrounding synovial fluid where can be intercepted by accompanying antibiotics.

Other medical implants, computing devices, and corresponding methods according to embodiments of the present disclosure will be or become apparent to one with skill in the art upon review of the following drawings and detailed description. It is intended that all such additional medical implants, computing devices, and methods be included within this description, be within the scope of the present inventive subject matter, and be protected by the accompanying claims. Moreover, it is intended that all embodiments disclosed herein can be implemented separately or combined in any way and/or combination.

DESCRIPTION OF THE DRAWINGS

Aspects of the present disclosure are illustrated by way of example and are not limited by the accompanying drawings. In the drawings.

DETAILED DESCRIPTION

Figure 1A:
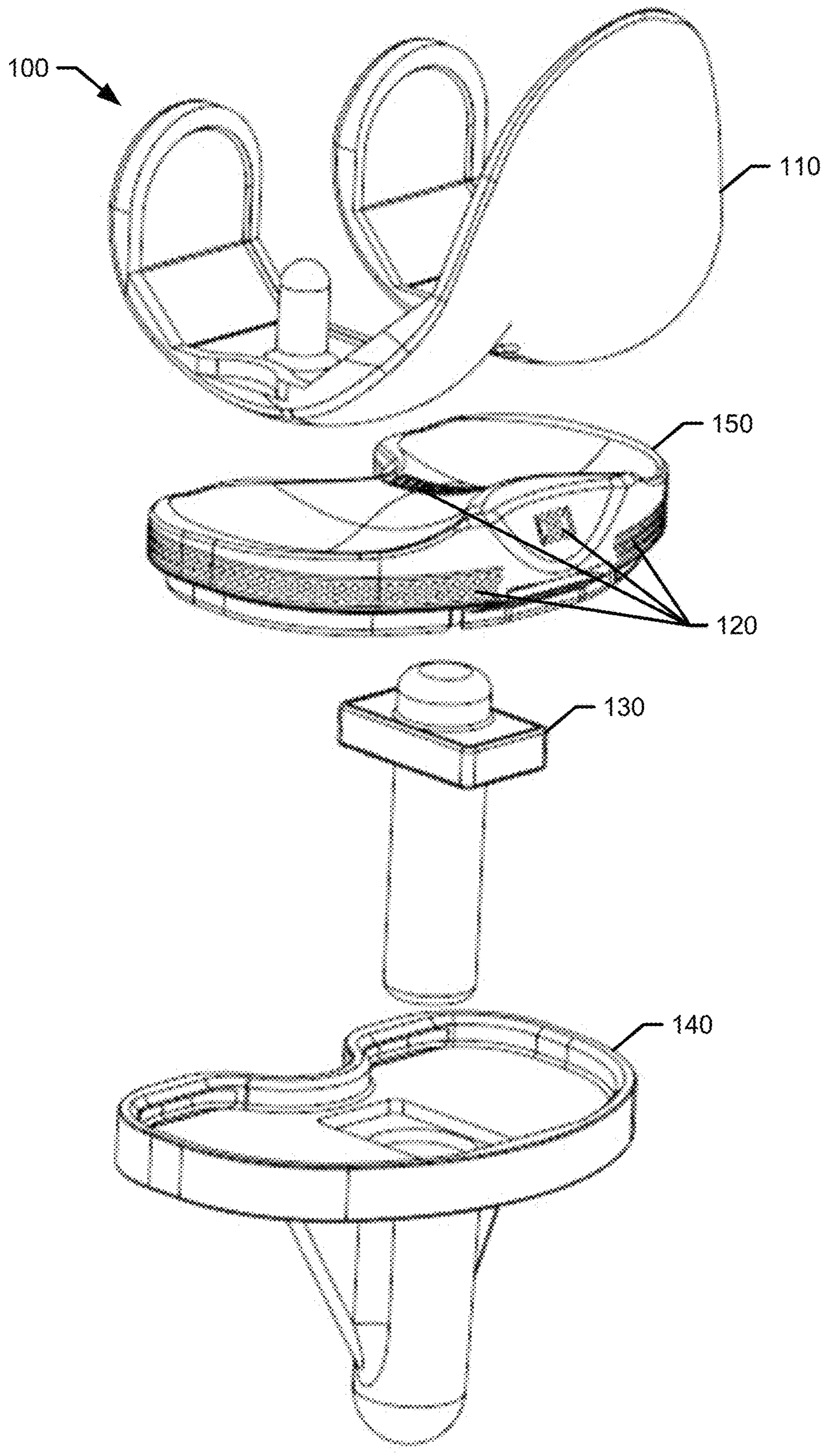
FIG. 1A illustrates an exploded isometric view of some components of a medical implant including a tibial insert, implant component, energy storage device, and tibial tray according to some embodiments of the present disclosure.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Some embodiments of the present disclosure are directed to joint reconstruction implants that have electronic circuits ("smart implants") which are operate to provide physicians and/or their patients the operational ability to prevent, monitor, detect, and diagnose Periprosthetic Joint Infection (PJI). Smart implants can be further operative to reduce or prevent and eradicate PJI through operation of the electronic circuits, and may increase the effectiveness of antibiotics and reduce the prevalence of two-stage revision procedures.

FIG. 1A illustrates an exploded isometric view of some components of a medical implant 100 including a tibial insert 110, implant component 150, energy storage device 130, and tibial tray 140 according to some embodiments of the present disclosure.

Referring to FIG. 1A, the medical implant 100 is a knee replacement implant. The implant component 150 may be housed between the tibial tray 140 and tibial insert 110 within cavities in each component. FIG. 1A is an implant construct for total knee arthroplasty, however, it should be noted that the present disclosure is directed to various embodiments in any orthopedic implant application including but not limited to partial knee arthroplasty, revision knee arthroplasty, total hip arthroplasty, intramedullary nailing, trauma plating, and spinal fusion.

The implant component 150 of the medical implant 100 may include at least one electrode array (e.g., electrode arrays 120) that is exposed to fluid and/or tissue of a patient that the medical implant is implanted in. For example, the implant component 150 includes two electrode arrays along the side of the implant component 150, a third electrode array on top of the implant component 150 that is facing upward, and a fourth electrode array that is towards the front of the implant component 150 and is facing in a tilted forward facing direction. While embodiments illustrate and describe specific placements of the electrode arrays, embodiments herein are not limited to such placements and can be on any surface of the medical implant 100 such as the implant component 150, tibial insert 110, and/or tibial tray 140. In preferred embodiments, the electrode arrays are placed in locations where there is minimal or no articular wear from the different components of the medical implant. For example, in locations where the different components of the medical implant do not contact each other while implanted in the patient.

The electrode arrays 120 may include at least two electrodes spaced apart on the implant component 150. In some embodiments, at least one of the electrodes is a sensor electrode that is configured to measure electrical and/or chemical characteristics. In some embodiments, the electrical and/or chemical characteristics indicate at least one of impedance, conductivity, temperature, oxygen, and potential hydrogen (pH).

In some embodiments, pH is measured by the working electrode(s) by measuring the change in pH level to obtain qualitative assessment of biofilm and its growth. For example, a voltage signal may be generated in response to change in the pH as biofilm grows. As biofilm grows, the biofilm may produce more pH byproducts. If the biofilm produces more acidic by products, this may lower the pH and provide a lower voltage response. If the biofilm produces more basic byproducts, this may increase the pH and provides a higher voltage response. If the biofilm produces both acidic and basic byproducts, this may alter the pH level based on the more dominant byproduct present and provide the respective voltage response.

In some embodiments, oxygen is measured by the working electrode(s) by a change in oxygen levels/concentrations to obtain qualitative assessment of the biofilm and its growth. For example, a current signal may be generated in response to change in oxygen level/concentrations as the biofilm grows. As the biofilm grows more oxygen molecules may be consumed by the bacteria for their metabolic processes. The extracellular matrix of the biofilm may become dense and thick and the pathways where the oxygen molecules travel becomes narrower making it harder for oxygen to travel to inner deep layers of the biofilm's medium. This may result in a depletion of oxygen molecules in the inner layers and most oxygen molecules may stay on the surface of biofilm's medium. With less available oxygen molecules in the inner layers of the extracellular matrix, there may be less redox reactions happening since redox reactions requires oxygen molecules. Redox reactions are reactions that involve transfer and movement of electrons between the biofilm and the working electrode. Less redox reactions may result in less electron transfer, which yields less electrical current flow in the system since electrical current is based on the rate of electric charges.

In some embodiments, conductivity is measured by the working electrode(s) by a change in conductivity to obtain quantitative assessment of biofilm and its growth. For example, a current signal is generated in response to change in conductivity as biofilm grows. As the biofilm grows, the biofilm may produce more extra polymeric substances (EPS) which enhances the conductive properties of biofilm's medium. This is due to proteins and other compounds that form this matrix of EPS, may create some conductive network within the biofilm's medium. This may result in the allowance for more movement of electrons. With more of these substances, the extracellular matrix can become more conductive, which increases the electrical current. It may depend on whether we have more of these conductive pathways being created or more of a complex structure with densely packed cells and thick extracellular matrix that acts as barrier to prevent electron flow, being created.

In some embodiments, impedance is measured by the working electrode(s) as a change in impedance, reflected as change in voltage corresponding to bacterial cell sizes to obtain quantitative assessment of biofilm and its growth. For example, a voltage signal is generated in response to the size of bacterial cells passing through the aperture that will alter the impedance as biofilm grows. As biofilm grows, the biofilm may produce more and/or larger biofilm particles such as bacterial cells that will enter through the aperture (that is designed to allow only biofilm particles to enter through while blocking out any fluid). As those charged particles (the bacterial cells) flows through the aperture and occupy the channels, they will disrupt and interrupt the flow of fluid (synovial or electrolyte solution) that was supposed to originally fill the channel in the first place. This obstruction/displacement of fluid in the channels may alter the impedance of the electrode array. This change in impedance may be detected/reflected as change in voltage across the electrode array where the magnitude of the voltage change corresponds to the size or concentration of the particles, which are the bacterial cells that entered through the aperture. Larger size and/or higher number (concentration) of particles/bacterial cells entering the aperture, as a result of increased biofilm growth may yield more impedance which translates to larger voltage change. Therefore, larger magnitude of voltage change may correspond to larger bacterial cell size and/or more concentration of it, which can be counted and quantified.

In some embodiments, the working electrode(s) act as temperature sensor or have temperature sensors connected thereto, in order to measure the temperature of the fluid/tissue in contact with the working electrode(s).

In some embodiments, the electrode arrays 120 are located on the surface of parts of the medical implant 100. In other embodiments, the electrode arrays 120 are embedded on the surface of components of the medical implant 100 and have at least two electrodes exposed to allow measuring of electrical and/or chemical characteristics.

In some embodiments, the medical implant 100 may include implant circuitry inside the implant component 150 that is operative to supply voltage to at least one of the sensor electrodes to measure electrical and/or chemical characteristics, and communicate signaling indicating the electrical and/or chemical characteristics through a wireless communication interface of the medical implant 100. For example, the signaling may be communicated from the medical implant (through the wireless communication interface) to a clinician for analysis and determinations on possible treatments based on the signaled indications of electrical and/or chemical characteristics.

In some embodiments, the implant component 150 is electrically connected to the energy storage device 130 and is primarily or fully powered by the energy storage device 130.

Figure 1B:
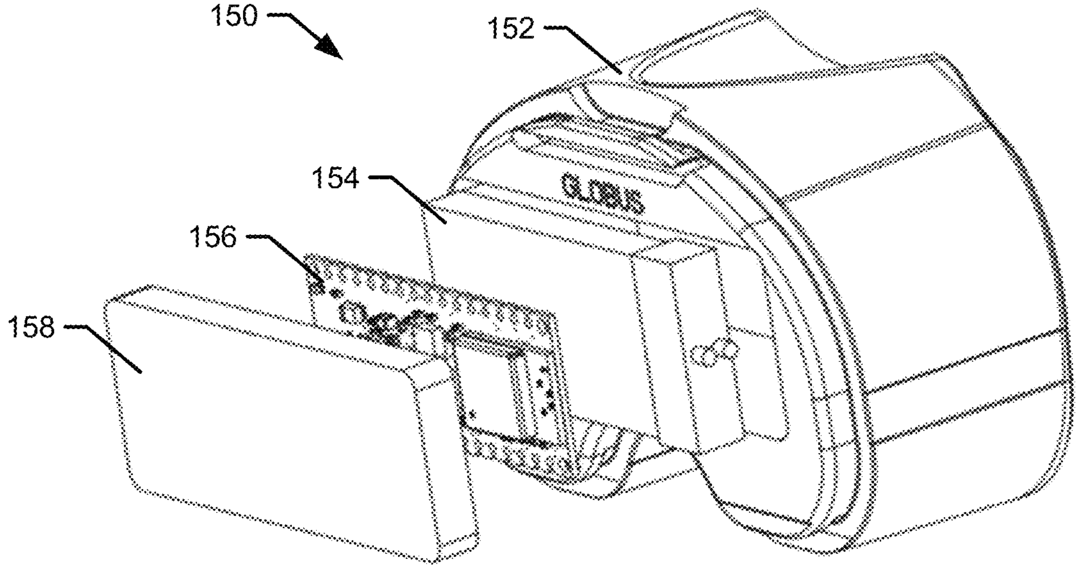
FIG. 1B illustrates an exploded isometric view of components of the implant component of the medical implant that is operative to supply voltage to at least one sensor electrode to measure electrical and/or chemical characteristics, according to some embodiments of the present disclosure.

FIG. 1B illustrates an exploded isometric view of components of the implant component of the medical implant that is operative to supply voltage to at least one sensor electrode to measure the electrical and/or chemical characteristics, according to some embodiments of the present disclosure.

Referring to FIG. 1B, the implant component 150 includes a support 152 that connects to (or forms part of) the tibial insert (e.g., tibial insert 110 of FIG. 1A) on which are mounted at least one electrode array comprising the at least two electrodes spaced apart on the implant component 150, an implant component energy storage device 154 (e.g., rechargeable battery or capacitive circuitry, that is additional to or alternative of the energy storage device 130), implant circuitry 156, and an enclosure 158 adapted to hermetically seal the implant circuitry 156 and implant component energy storage device 154 to the support 152 while implanted in the patient.

Figure 1C:
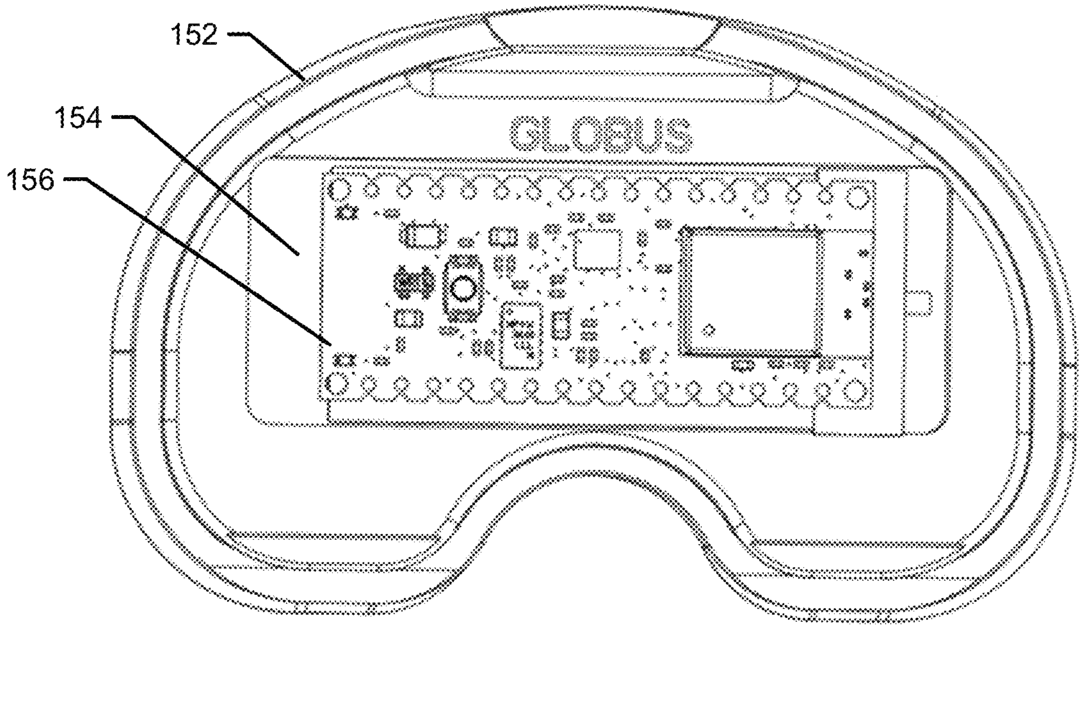
FIG. 1C illustrates a top view of the implant component of the tibial insert of FIG. 1B showing implant circuitry including a power management unit and a controller which are operative according to some embodiments of the present disclosure.

FIG. 1C illustrates a top view of the implant component of the tibial insert of FIG. 1B showing implant circuitry 156 which is operative to at least supply voltage (from implant component energy storage device 154 and/or energy storage device 130 of FIG. 1A) to at least one of the sensor electrodes to measure electrical and/or chemical characteristics, and communicate signaling based on the measured electrical and/or chemical characteristics through a wireless communication interface of the medical implant. In some embodiments, the implant circuitry 156 is powered primarily or fully by the energy storage device 130 of FIG. 1A. In embodiments where the energy storage device 130 is the primary source of power, the implant component energy storage device 154 acts as secondary or back-up power source.

Implant circuitry 156 may include one or more processor circuits ("processor") which execute instructions stored in one or more memory circuits ("memory").

In some embodiments, the electrodes in the electrode arrays 120 are electrically connected to the implant component 150 through insulated electrical traces or wires routed on the surface of the implant component 150 or through the body of the implant component 150. The electrical traces or wires may terminate at connectors that interface with pass-through connectors of the implant component 150. The housing (or support 152) of the implant component (along with other parts of the medical implant) may be constructed at least in part of a material that minimizes RF interference. In some embodiment, the top portions of the housing are constructed of a RF transparent material such as PEEK to allow transmission of the radio waves. In some embodiments, the bottom component of the housing could be constructed of an RF transparent material such as PEEK or an RF shielding material such as TAV (titanium).

In some embodiments, the implant circuitry is a printed circuit assembly (PCA). The PCA may include electronic components and circuitry required for communication, wireless charging, sensing, and stimulation, including the RF antenna(s).

Figure 2A:
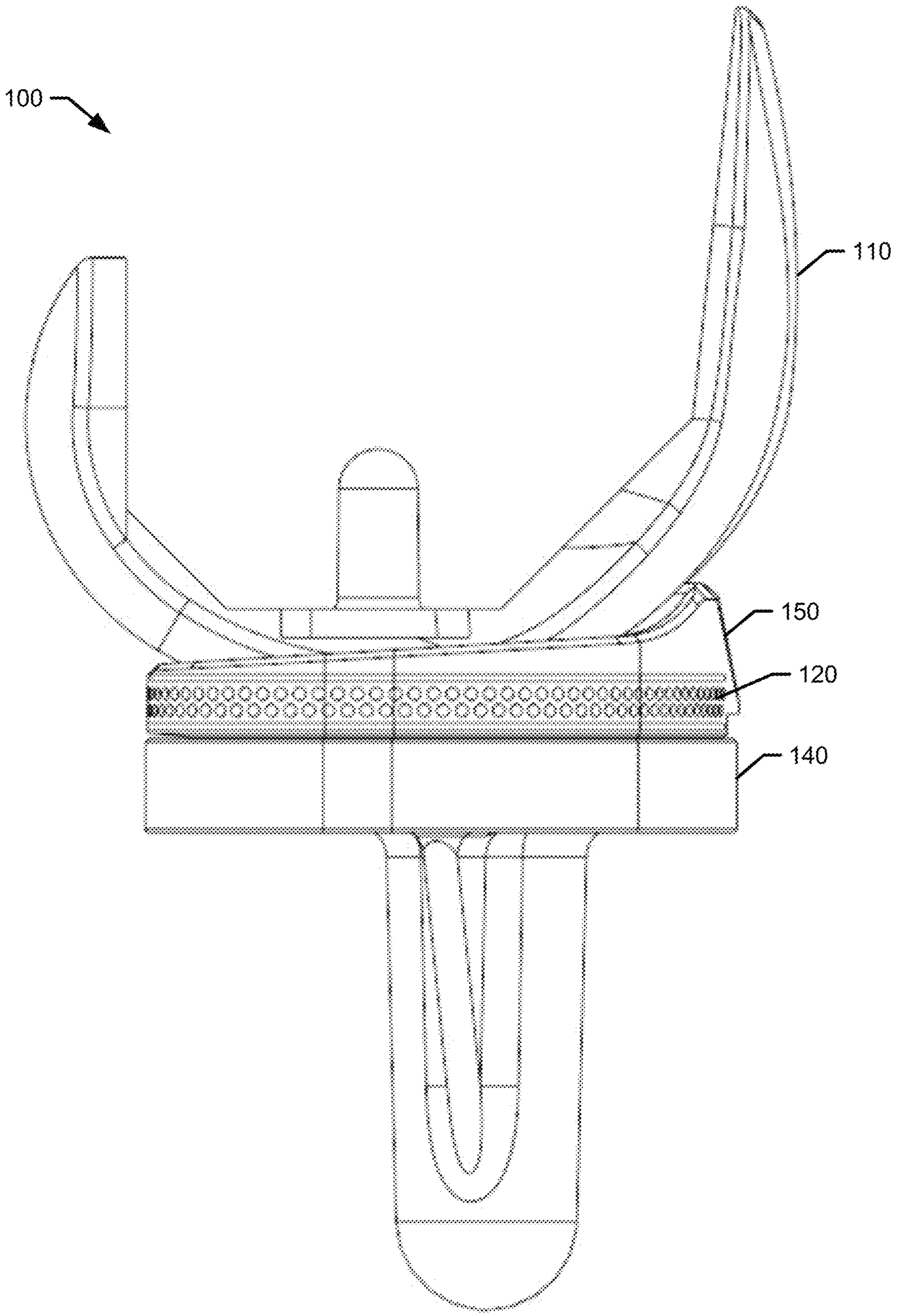
FIG. 2A illustrates a side view of the medical implant showing the tibial insert, implant component, and tibial tray physically connected, according to some embodiments of the present disclosure.

FIG. 2A illustrates a side view of medical implant 100 showing the tibial insert 110, implant component 150, and tibial tray 140 physically connected, according to some embodiments of the present disclosure. The implant component 150 includes a single electrode array 120 visible.

Figure 2B:
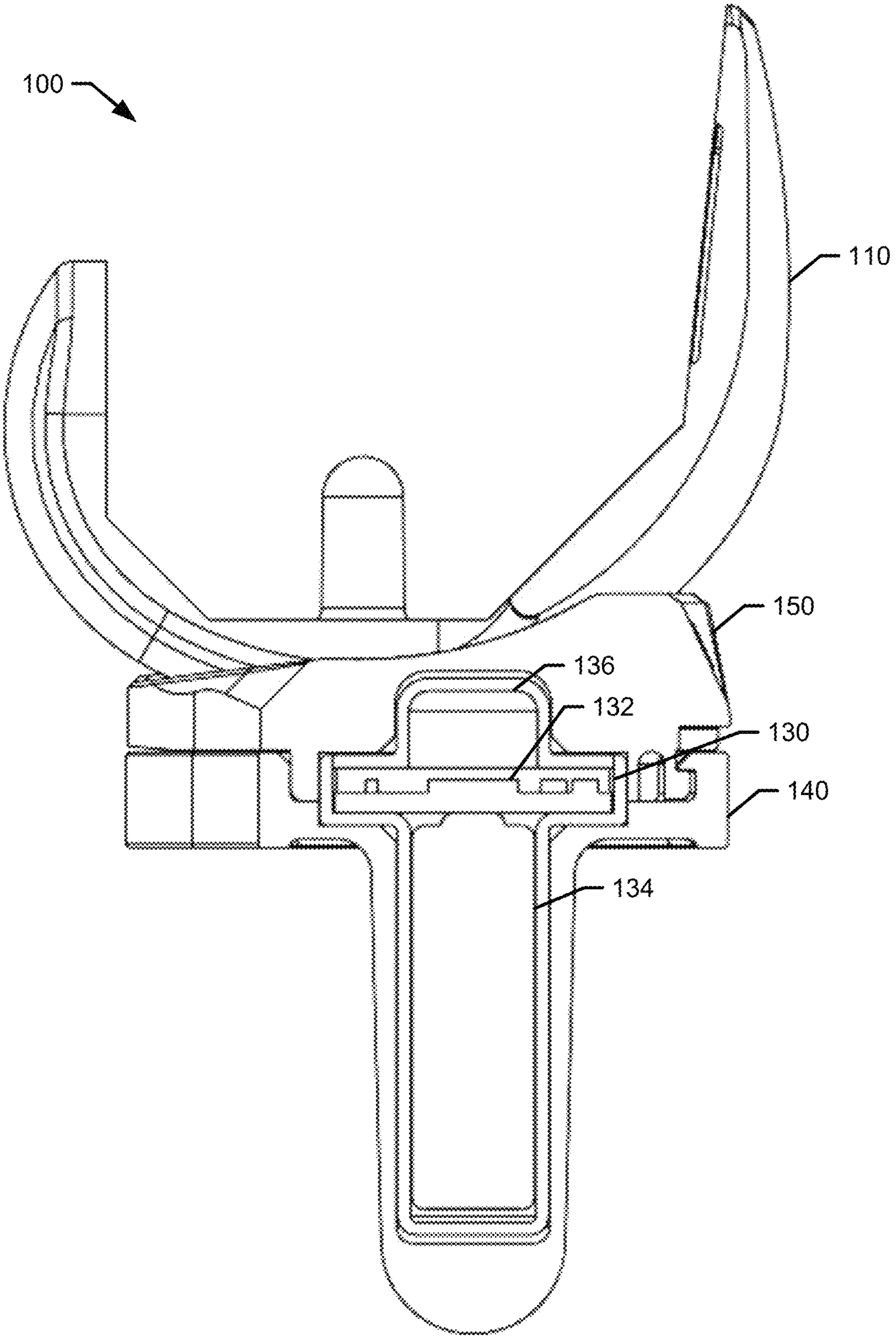
FIG. 2B illustrates the medical implant of FIG. 2A with the enclosures removed to expose an arrangement of the embedded energy storage device and electronics including a circuit board, a power management unit, controller, and sensors according to some embodiments of the present disclosure.

FIG. 2B illustrates the medical implant 100 of FIG. 2A with the enclosures removed to expose an arrangement of the embedded energy storage device 130 and electronics 132 including a circuit board, a power management unit, controller, and sensors according to some embodiments of the present disclosure. In some embodiments, the electronics 132 may perform the operations of the implant circuitry 156 or be in communication with the implant circuitry 156 to provide the power from a power resource 134 (e.g., rechargeable battery or capacitive circuitry) to other components of the medical implant (e.g., the electrode array(s)) through the component 136.

Figure 2C:
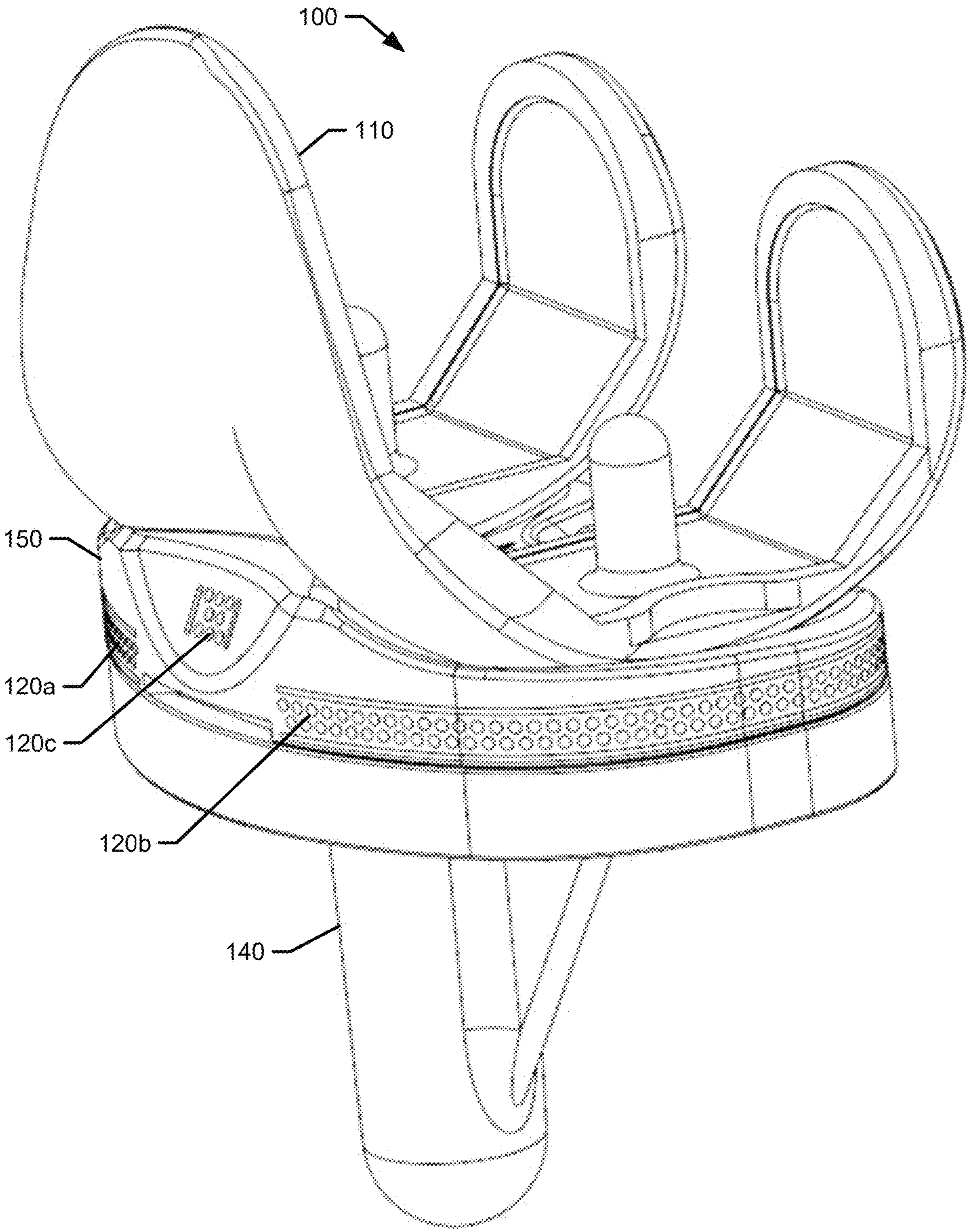
FIG. 2C illustrates another view of the medical implant with two electrode arrays on either side of the implant component and a third electrode array centrally located on a frontward face of the implant component, according to some embodiments of the present disclosure.

FIG. 2C illustrates another view of the medical implant 100 with two electrode arrays 120*a-b* along the side of the implant component 150 and a third electrode array 120*c* centrally located on a frontward face of the implant component, according to some embodiments of the present disclosure.

Figure 2D:
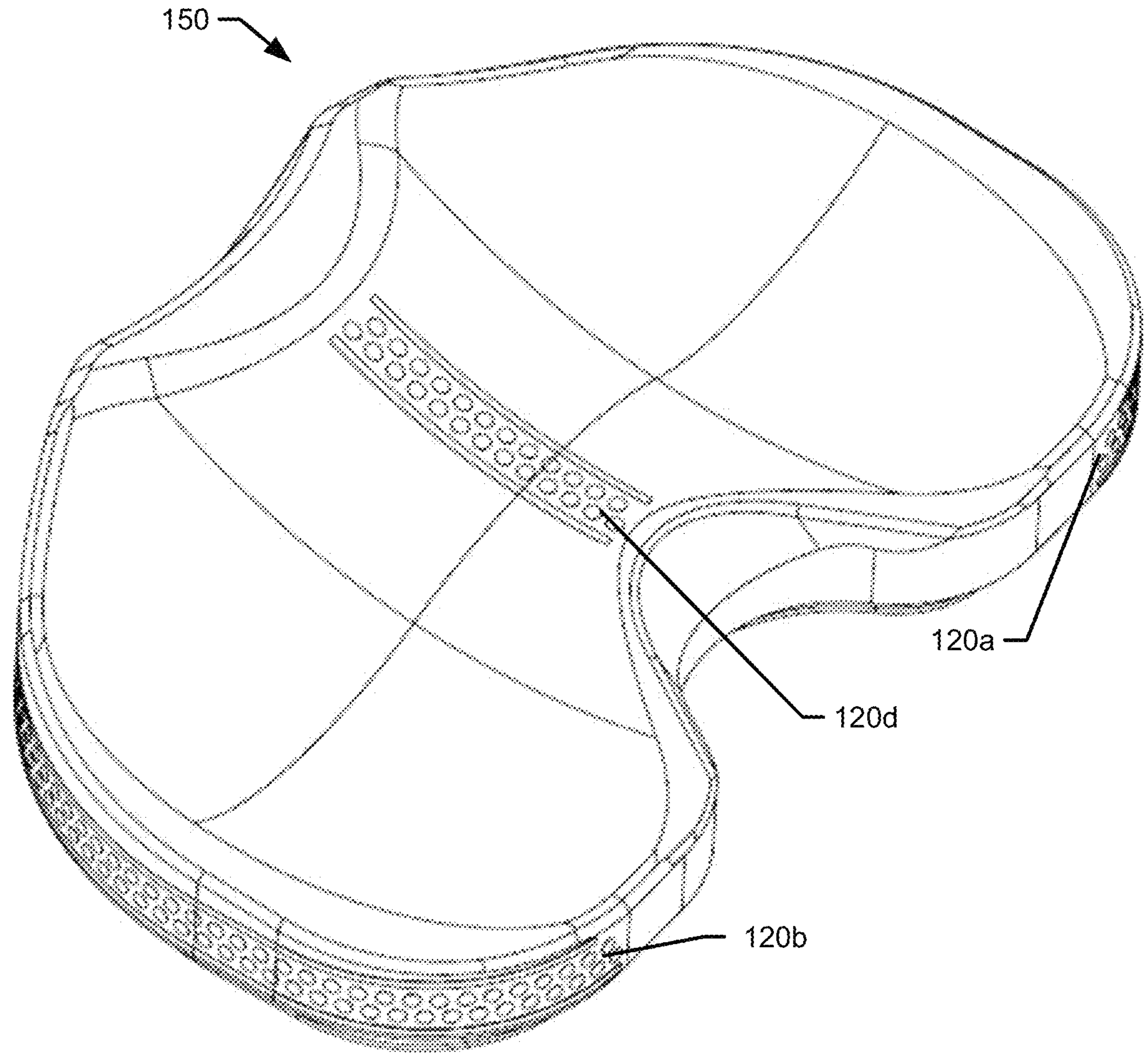
FIG. 2D illustrates the implant component with two electrode arrays on either side of the implant component and a third electrode array centrally located on a top of the implant component, according to some embodiments of the present disclosure.

FIG. 2D illustrates the implant component 150 with two electrode arrays 120*a-b* along the side of the implant component 150 and a third electrode array 120*d* centrally located on a top of the implant component 150, according to some embodiments of the present disclosure. In some embodiments, the third electrode array 120*d* is centrally located on top of the implant component 150 in order to not be in contact with the tibial insert 110 of FIG. 2C while the implant is in use by a patient.

Figure 2E:
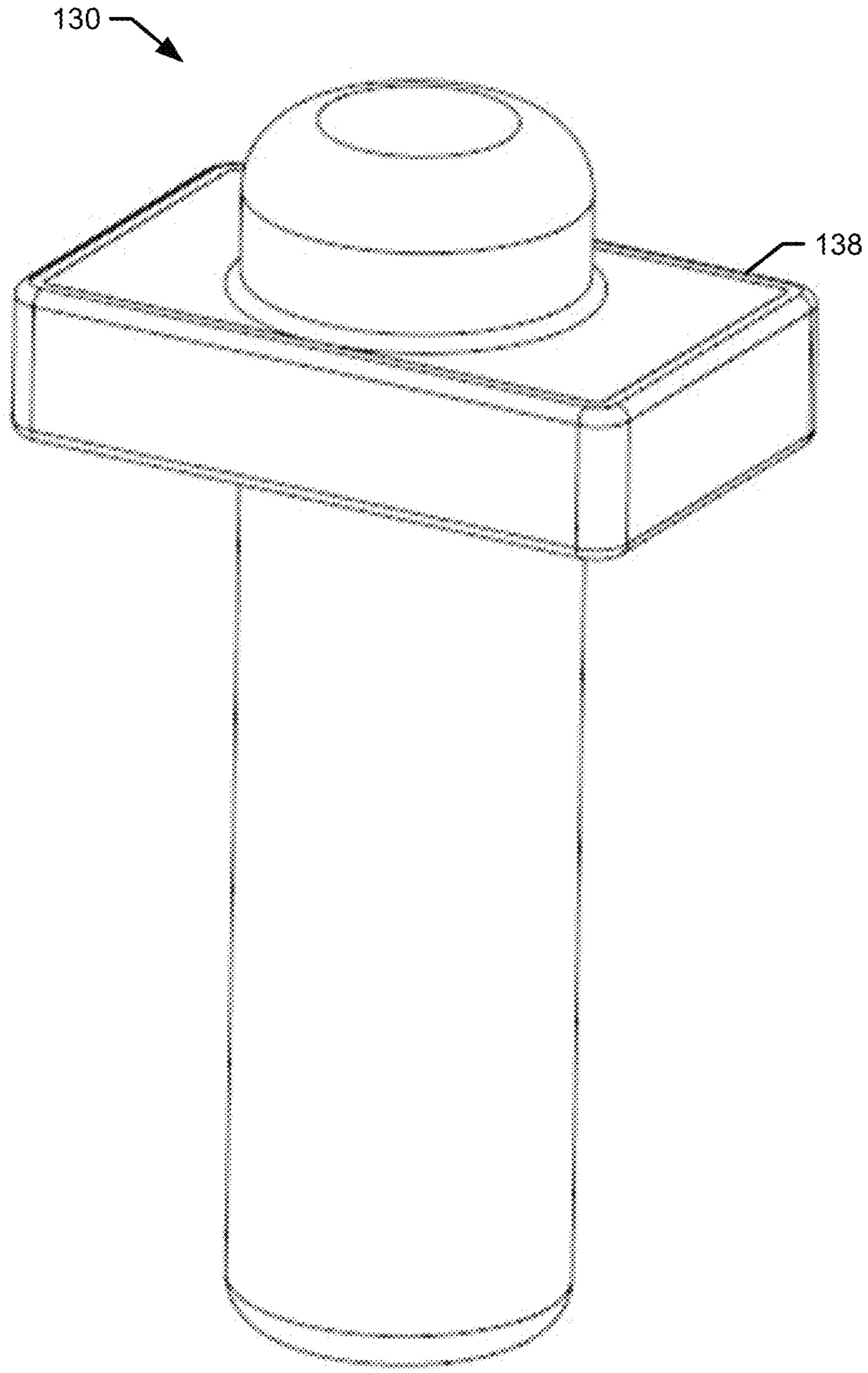
FIG. 2E illustrates the energy storage device of the medical implant, according to some embodiments of the present disclosure.

FIG. 2E illustrates the energy storage device 130 of the medical implant, according to some embodiments of the present disclosure. In some embodiments, the energy storage device 130 includes an enclosure 138 that hermetically seals the power resource, electronics, and component 136, but allows for power transfer from the power resource to other components of the medical implant.

Figure 2F:
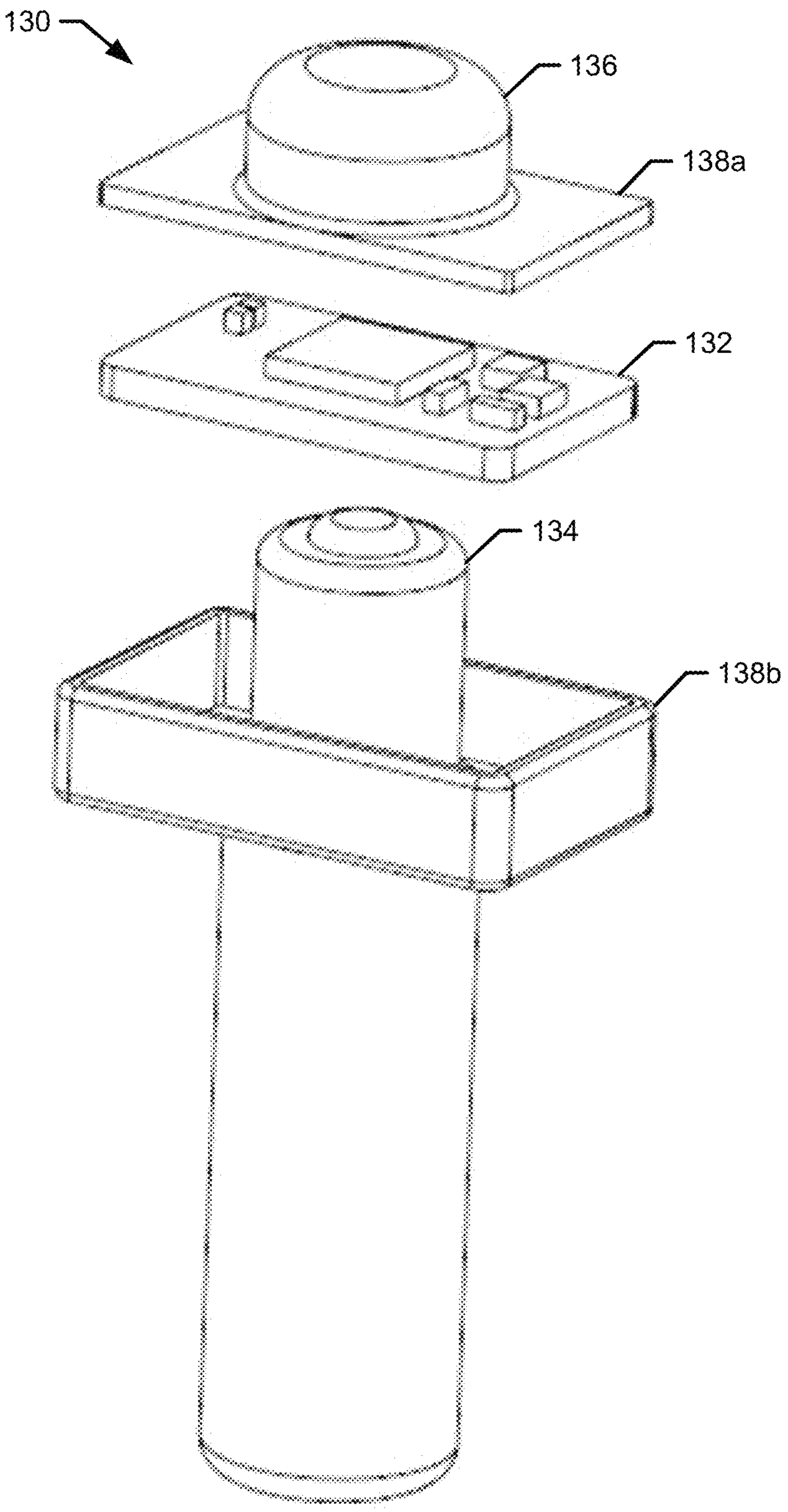
FIG. 2F illustrates an exploded isometric view of the energy storage device and electronics including a power management unit, controller, and sensors according to some embodiments of the present disclosure.

FIG. 2F illustrates an exploded isometric view of the energy storage device 130 and electronics 132 including a power management unit, controller, and sensors according to some embodiments of the present disclosure. In this view, the enclosure is separated apart such that enclosure 138*a* is detached from enclosure 138*b*.

Figure 3:
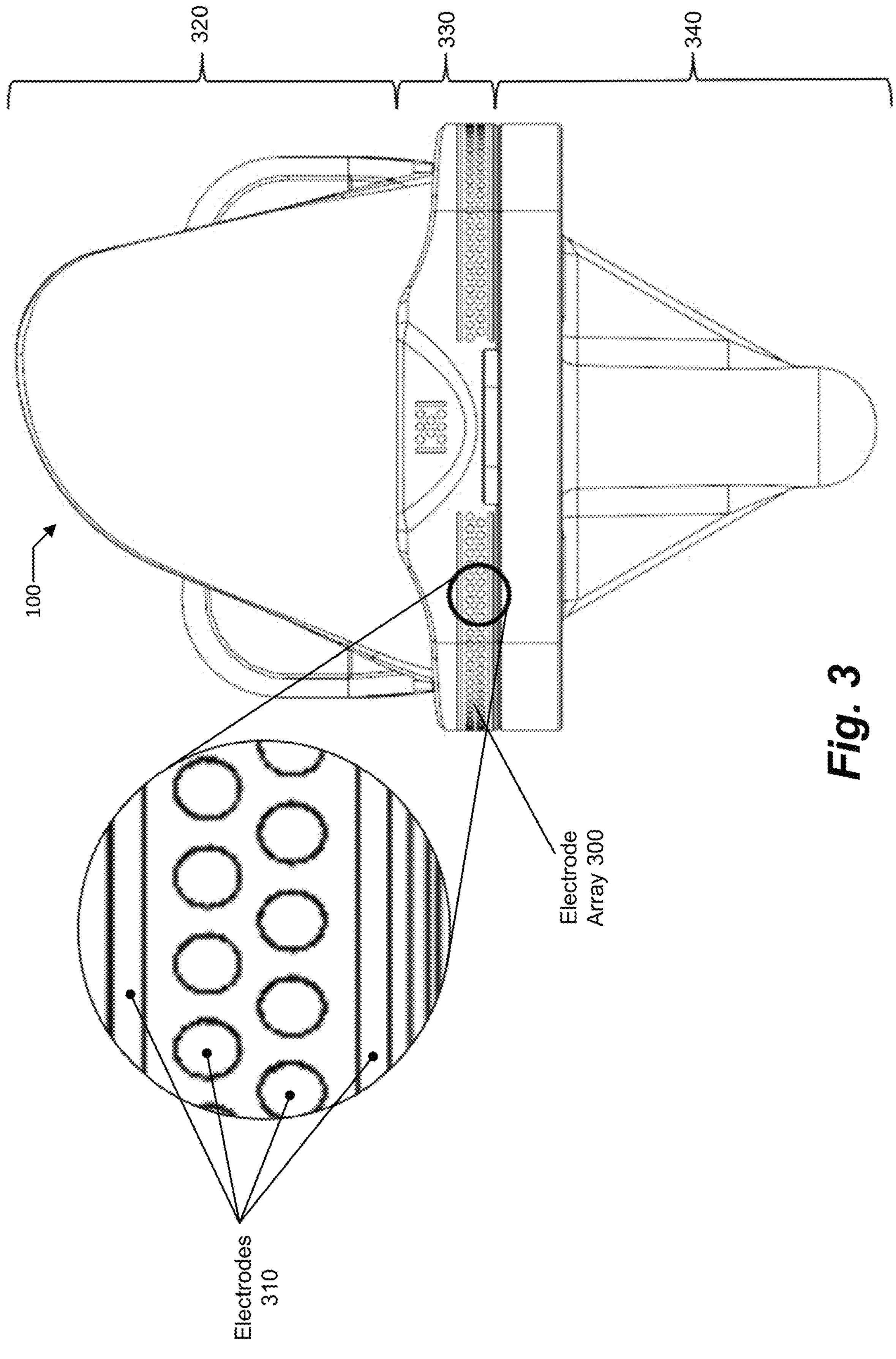
FIG. 3 illustrates a front view of the medical implant which includes a magnified view of one of the electrode arrays of the implant component, according to some embodiments of the present disclosure.

FIG. 3 illustrates a front view of medical implant 100 which includes a magnified view of one of the electrode arrays of the implant component, according to some embodiments of the present disclosure. The magnified view of electrode array 300 shows an arrangement of electrodes 310 spaced apart on the implant component. Additionally, portions of the medical implant are illustrated. Portion 320 illustrates the femoral component of the medical implant 100, portion 330 illustrates the tibial insert of the medical implant 100, and portion 340 illustrates the tibial tray of the medical implant 100.

Figure 4A:
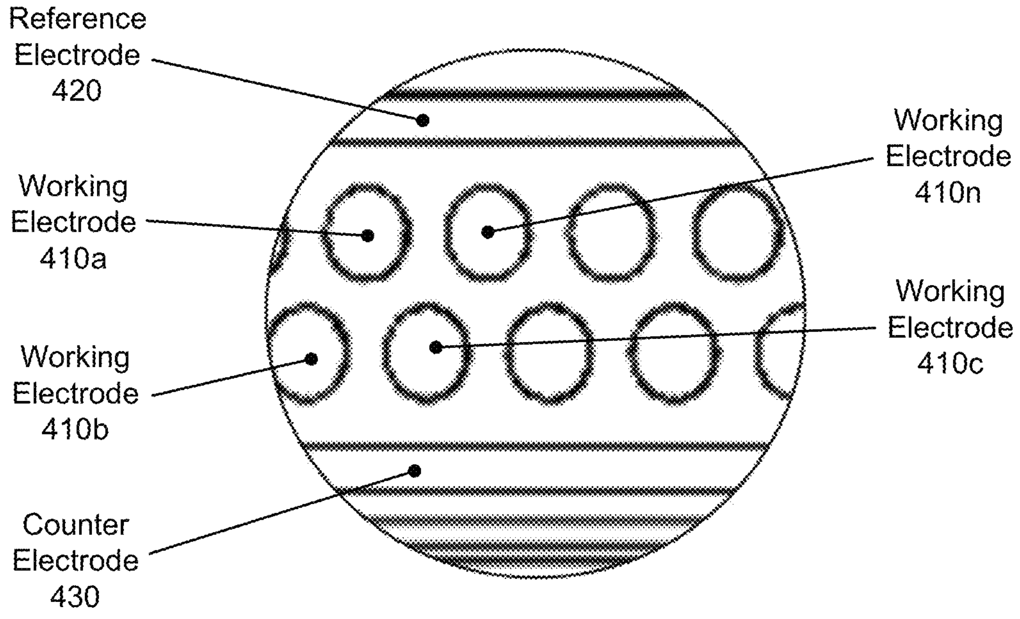
FIG. 4A illustrates a magnified view of the electrode array of the medical implant including a reference electrode, a plurality of working electrodes, and a counter electrode, according to some embodiments of the present disclosure.

FIG. 4A illustrates a magnified view of the electrode array of the medical implant including a reference electrode 420, a plurality of working electrodes 410*a-n*, and a counter electrode 430, according to some embodiments of the present disclosure.

In some embodiments of the present disclosure, the working electrodes 410*a-n* are sensor electrodes—capable of measuring and/or detecting electrical and/or chemical characteristics or a type of bacteria—and/or stimulation electrodes—capable of being electrically stimulated by current supplied by the energy storage device to be at a level which reduces the biofilm on at least part of the implant component while implanted in the patient.

The electrode material may include, but is not limited to, at least one of silver, silver chloride, gold, platinum, graphene, graphite, conducting polymers, or a combination thereof.

In some embodiments, the working electrodes of an electrode array are identical electrodes which are used for any combination of measuring electrical and/or chemical characteristics and electrical stimulation functions.

In some other embodiments, the working electrodes of an electrode array include an arrangement of specialized electrodes for various measuring of electrical and/or chemical characteristics and electrical stimulation functions.

In some embodiments, electrode arrays are included in 3-electrode systems with a reference electrode, working electrode, and counter electrode. In some embodiments, an upper linear electrode could function as the reference electrode (e.g., reference electrode 420), the middle circular electrodes could function as the working electrodes (e.g., working electrodes 410*a-n*), and the lower linear electrode could function as the counter electrode (e.g., counter electrode 430).

In some embodiments, the reference electrode 420 is an electrode that is supplied a fixed reference voltage (e.g., 1.7 volts) for the sensing measurements. For example, reference electrode 420 may provide a baseline against which the changes in potential at the working electrode(s) can be interpreted. By maintaining a stable and reproducible reference potential through the reference electrode, the electrode array may get more consistent electric signal response measurements so it is easier to analyze and interpret the electrical and/or chemical characteristics measured by the working electrodes.

In other embodiments, the reference electrode 420 is not used (or is not present) on the electrode array. In yet other embodiments, the reference electrode 420 is connected to the counter electrode thereby making them both act as counter electrodes. How the reference electrode is used may depend on the type of electrical and/or chemical characteristic that is being measured by the working electrode(s) or the measuring process used (e.g., amperometry).

The counter electrode 430 acts as the cathode in the three-electrode array system illustrated in these Figures.

The working electrode acts as the anode in the three electrode array system illustrated in these Figures, and is where the sensor measurements take place. For example, the working electrodes could be utilized for spatial mapping of a single parameter, such as impedance measurement, yielding an impedance measurement at each working electrode on the electrode array. Using multiple electrochemical techniques in series, such as potentiometry, electrochemical impedance spectrometry, and cyclic voltammetry, the array of working electrodes may also be used to capture multiple characteristic readings sequentially, such as impedance, conductivity, and pH. However, in some embodiments, different electrochemical techniques could be performed on individual working electrodes in parallel. For example, cyclic voltammetry could be performed on working electrode 410*a*, amperometry could be performed on working electrode 410*b*, and impedance spectroscopy could be performed on electrode 410*c*. The individual working electrodes could be grouped into a set of electrodes that are repeated to form an electrode array on the surface of the implant (discussed in more detail below).

Regarding the electrical stimulation of the working electrodes, the implant circuitry may be operative to control electrical stimulation of specific working electrodes, or all the working electrodes of an electrode array, by current supplied by the energy storage device to be at a level which at least reduces formation of a biofilm on at least part of the implant component while implanted in the patient. The implant circuitry may provide a voltage differential between a working electrode(s) and a counter electrode to cause electric field(s) to extend therebetween, and controls the level of current density therebetween to at least reduce formation of a biofilm and/or to at least partially eradicate a biofilm on at least part of the implant component while implanted in the patient. The counter electrode may be the counter electrode in the same electrode array or a counter electrode of a different electrode array than the one in which the working electrode(s) are being stimulated at. Alternatively, there may be a counter electrode that is not a part of an electrode array that is used while a working electrode(s) is stimulated.

Figure 4B:
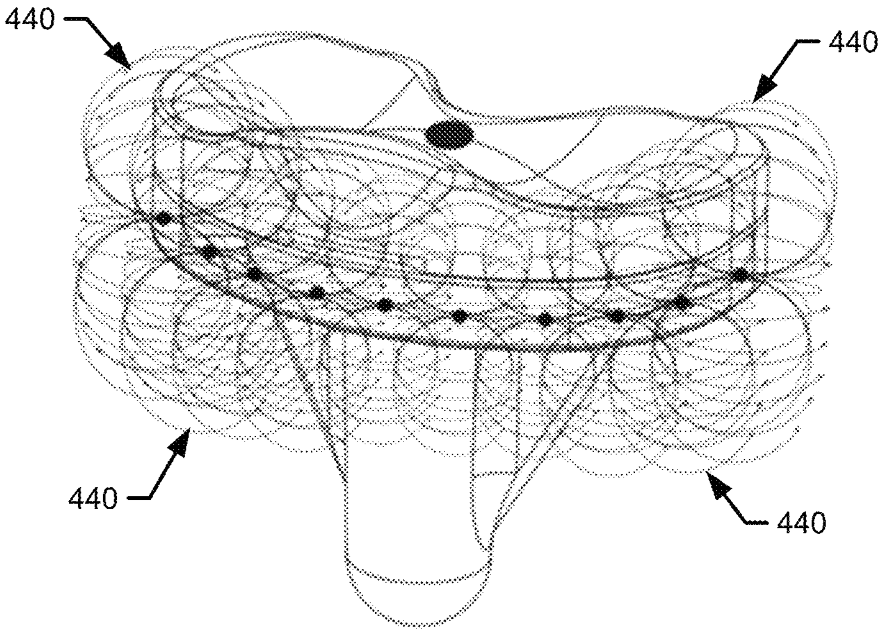
FIG. 4B illustrates electrical fields extending between the working electrodes and the counter electrode on the side surface while the electrode array of FIG. 4A is electrically stimulated, according to some embodiments of the present disclosure.

FIG. 4B illustrates electrical fields 440 extending between the working electrodes and the counter electrode on the side surface while the electrode array of FIG. 4A is electrically stimulated, according to some embodiments of the present disclosure.

Figure 4C:
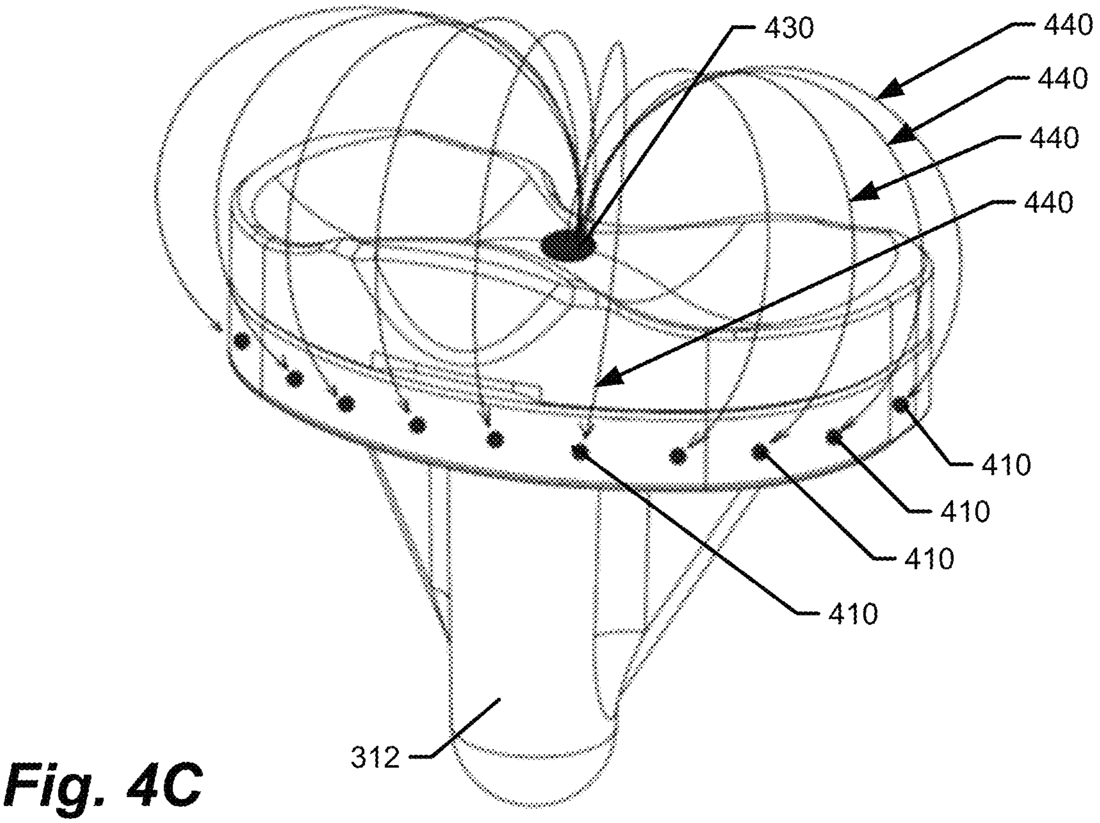
FIG. 4C illustrates electrical fields extending between the working electrodes on the side surface of the medical implant and a centrally located counter electrode on the implant component while the electrode array is electrically stimulated, according to some embodiments of the present disclosure.
Figure 5A:
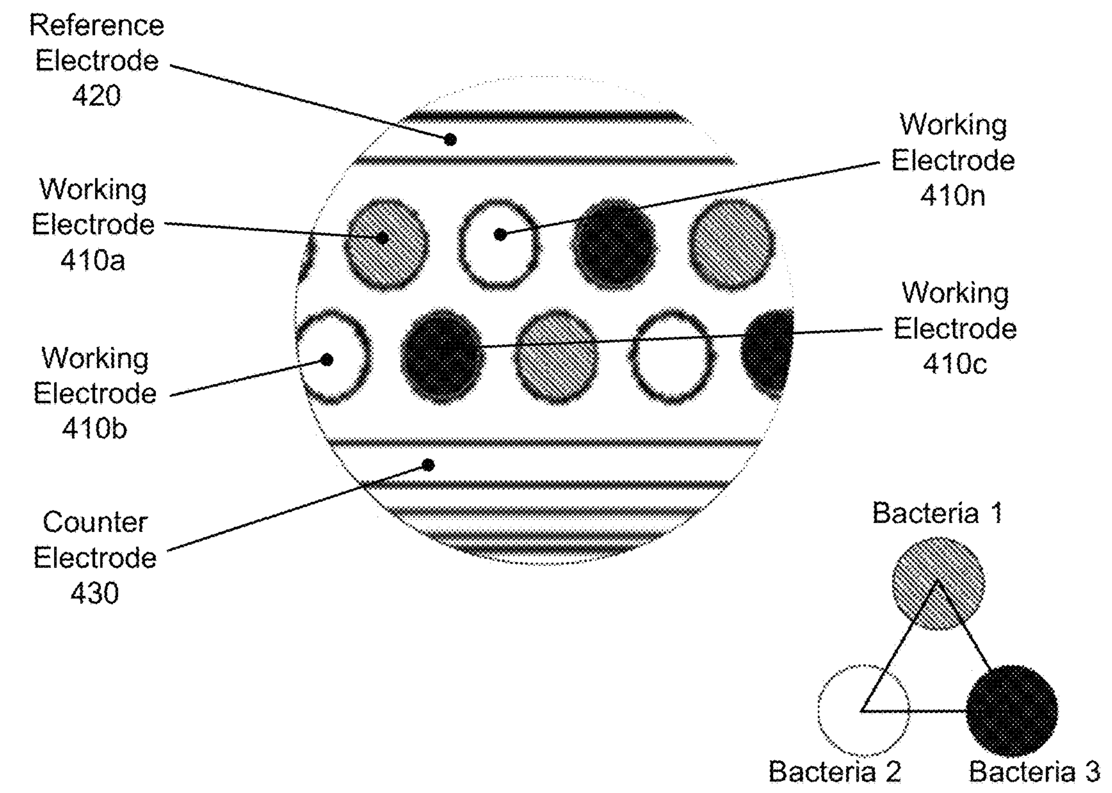
FIG. 5A illustrates another magnified view of the electrode array where the working electrodes are configured to measure or detect different types of bacteria, according to some embodiments of the present disclosure.

FIG. 4C illustrates electrical fields extending between the electrodes on the side surface and the centrally located electrode while the electrode array is electrically stimulated, according to some embodiments of the present disclosure FIG. 5A illustrates another magnified view of the electrode array where the working electrodes 410*a-n* are configured to measure or detect different types of bacteria or biofilm, according to some embodiments of the present disclosure. Some examples of types of bacteria that may be measured or detected by the working electrodes include, but are not limited to, *Staphylococcus aureus, Staphylococcus epidermidis*, and *Streptococcus*. For example, in FIG. 5A, the electrode array has sets of uniquely functionalized working electrodes. The working electrodes could be functionalized with antibodies to detect specific bacterial species. For example, the working electrode may have a functionalization layer on top of the electrode and then a bio-recognition element (e.g., enzyme, antibody, cell, and/or nucleic acid) on top the functionalization layer that allows the sensor electrode to detect or measure a specific electrical and/or chemical characteristic of the bacteria once it binds to the bio-recognition element on the working electrode.

In the example of FIG. 5A, the electrode array has sets of three working electrodes 410*a-c*, where each working electrode detects the presence of a unique bacterial species, such as *Staphylococcus aureus, Staphylococcus epidermidis*, and *Streptococcus*. While a set of three working electrodes is exemplified, it is noted that in some embodiments a set may include two or more working electrodes. In some embodiments, the different sets of working electrodes may overlap by at least one working electrode.

Additionally, in some embodiments, the working electrodes 410*a-n* may be configured to detect more than one type of bacteria or biofilm.

Figure 5B:
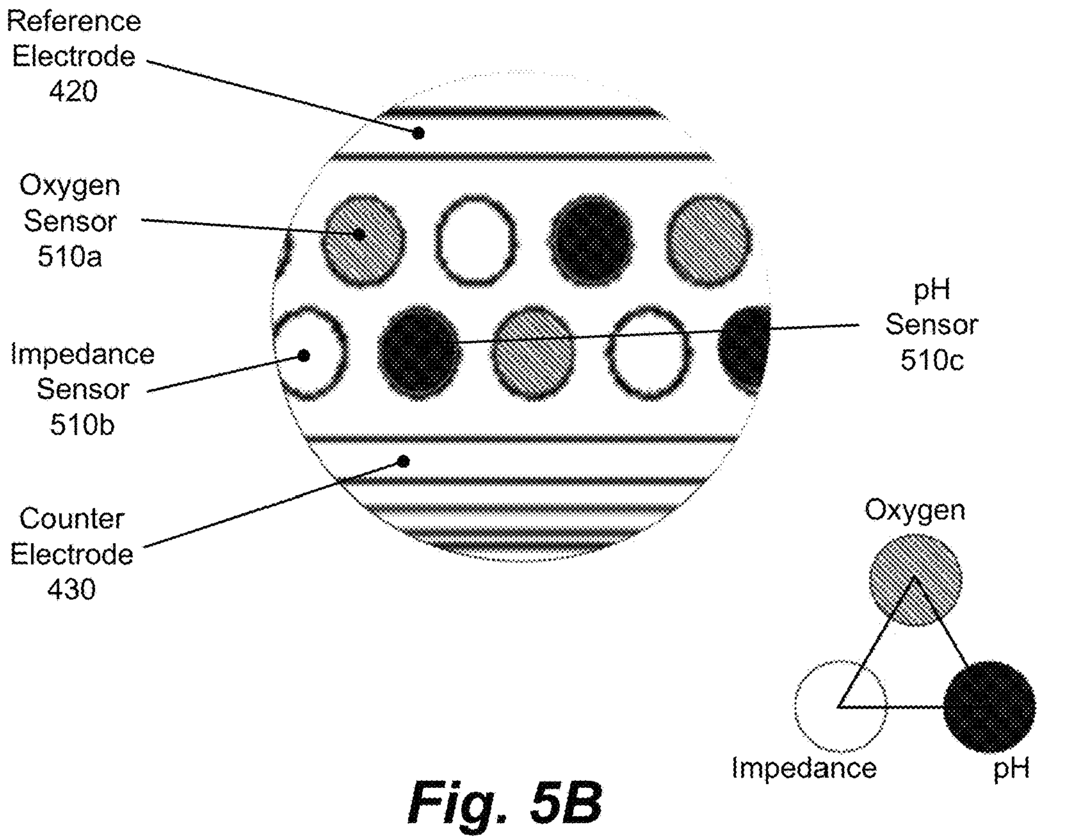
FIG. 5B illustrates yet another magnified view of the electrode array where each working electrodes is configured as an oxygen sensor, impedance sensor, or a potential hydrogen (pH) sensor, according to some embodiments of the present disclosure.

FIG. 5B illustrates yet another magnified view of the electrode array where each working electrode is configured as an oxygen sensor, impedance sensor, or a potential hydrogen (pH) sensor, according to some embodiments of the present disclosure. In this embodiment, the electrode array has sets of uniquely functionalized working electrodes to determine specific electrical and/or chemical characteristics which are correlative with the formation of bacterial biofilm. For example, each set can include an oxygen sensor 510*a*, impedance sensor 510*b*, and pH sensor 510*c*.

Additionally, in some embodiments, the working electrodes 510*a-c* may be configured to measure more than one type of electrical and/or chemical characteristic.

In some embodiments, the electrode array has any combination of working electrodes where at least one working electrode (or set of working electrodes) is configured to measure electrical and/or chemical characteristics and another at least one working electrode (or another set of working electrodes) is configured to detect a type of bacteria or biofilm.

When no biofilm is present, the average readings/measurements of each sensor electrode type across the electrode array may provide a characterization of the macro environment, namely the synovial fluid that surrounds the prosthetic joint. While certain parameters/characteristics, such as dissolved oxygen and impedance may not always have direct clinical relevance, the synovial fluid pH may be helpful in providing the clinician knowledge of the healing process and development of complications. For example, the synovial fluid pH from patients with periprosthetic joint infections typically ranges lower than normal, between 6 and 7.2. Normal pH is typically considered between 7.3 and 7.8.

Biofilm typically forms non-uniformly in one or more spots on the surface of the implant where planktonic bacterial attachment is preferential due to surface roughness or other factors. In some embodiments, the working electrodes could be intentionally designed to serve as the preferential attachment surface for planktonic bacteria, thereby increasing the probability that a bacterial biofilm forms on the sensor array rather than a non-instrumented portion of the implant surface. For example, the working electrodes and/or the surfaces surrounding the working electrodes may be configured to have a rougher surface than the rest of the medical implant in order to create a more preferential attachments surface for the bacteria to form than the rest of the medical implant.

Figure 6:
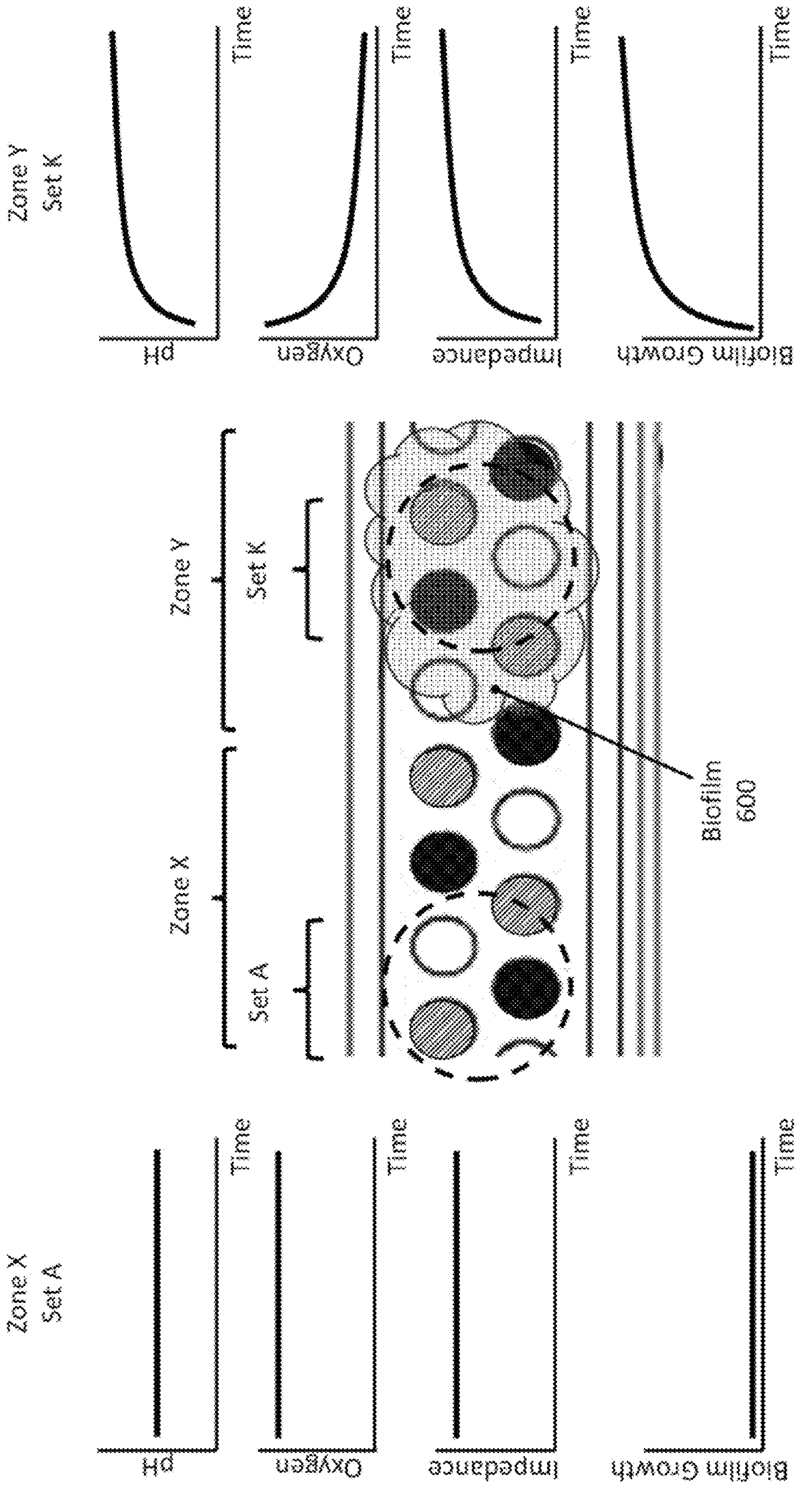
FIG. 6 illustrates a view of the electrode array with biofilm built up on the electrode array, and the electrode array is divided into sets and zones of electrodes, according to some embodiments of the present disclosure.

FIG. 6 illustrates a view of the electrode array with biofilm built up on the electrode array, and the electrode array is divided into sets and zones of electrodes, according to some embodiments of the present disclosure.

Referring to FIG. 6, if a biofilm forms on one or more electrodes (or set(s) of electrodes, for example Set K), the measurements of electrical and/or chemical characteristics from those electrodes could indicate the presence of biofilm as well as characterization of the biofilm growth state. For example, calibration curves, correlations, and/or machine learning models could be developed using in vitro and in vivo testing to relate the readings of electrochemical sensors with the presence and amount of biofilm on those sensors. For one such bacterial biofilm, the measured pH and impedance might increase while the oxygen decreases with the increase in biofilm growth. The combination of more than one type of sensor may allow for more robust and reliable correlations with biofilm growth.

By comparing localized readings from one or more sets of sensors with other sets of sensors or the average of all sensor readings, the implant component (e.g., implant component 150) or a computing device (discussed in more detail below) can indicate the specific location of biofilm growth on the implant surface. For example, multiple sets of sensor electrodes may be arranged in zones (e.g., Zone X and Zone Y) around the medical implant. The sensor electrodes in Set A within Zone X measure the electrical and/or chemical characteristics of the synovial fluid that contacts these sensor electrodes directly due to the lack of biofilm in growth in this area. Other sets within Zone X should provide readings/measurements that are consistent with Set A since all the sensor electrodes in the zone are in contact with the same synovial fluid, with no biofilm present. If the sensor electrodes in Set K within Zone Y are in contact with a bacterial biofilm, the sensor electrodes will yield readings/measurements that are indicative of biofilm formation. The readings/measurements of Set K could then be compared to the readings of Set A to indicate that a biofilm is present specifically in Zone Y, which maps to a specific location of the implant surface. This localized biofilm detection information could then be used to inform the clinician of the specific location of the biofilm growth. This information could then be utilized to perform targeted electrical stimulation to help remove or eradicate the biofilm altogether. After the stimulation treatment is administered, the measurement from the sensor electrodes in Set K may match readings to Set A and all other sets, indicating that the biofilm is removed and only the synovial fluid is in contact with the electrode array.

Figure 7:
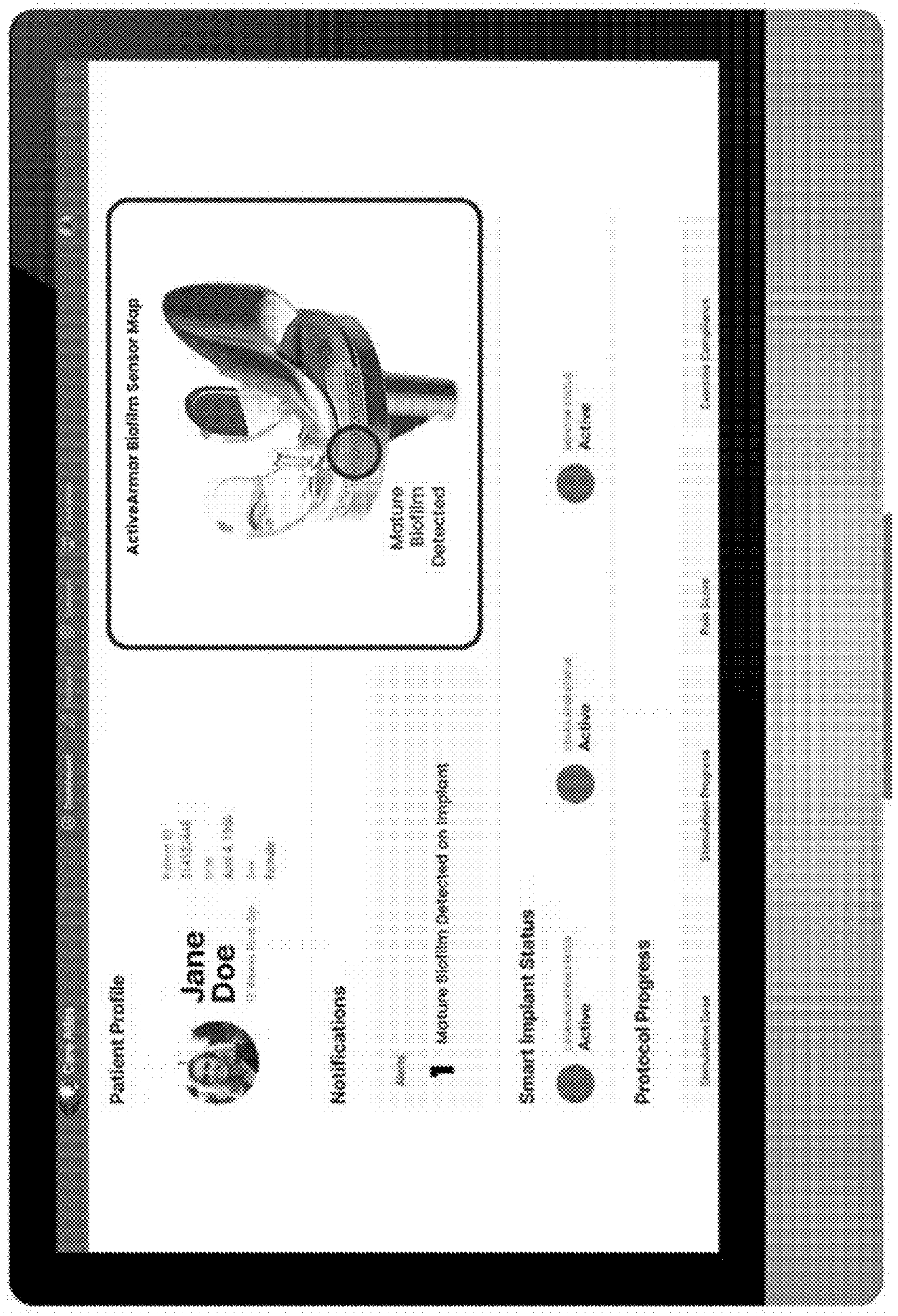
FIG. 7 illustrates an example clinician dashboard that depicts information received from the medical implant, according to some embodiments of the present disclosure.

FIG. 7 illustrates an example clinician dashboard that depicts information received from the medical implant, according to some embodiments of the present disclosure. In this example, the medical implant may communicate signaling indicating the electrical and/or chemical characteristics, that was measured by sensor electrodes of the medical implant, through the wireless communication interface to the computing device. The computing device is a device which is remotely located outside the body of the patient to receive signaling such as a smart phone, laptop or a desktop computer located nearby. The signaling may also indicate at least one of patient information that identifies the patient, a location of the sensor electrodes (or electrode arrays) from where the electrical and/or chemical characteristics were measured, whether biofilm is detected, a battery level of the energy storage device within the medical implant, and or other information relating to an operation or function of the medical implant.

The computing device may then process the received signaling and display a clinician dashboard similar to the clinician dashboard shown in FIG. 7, to allow the clinician to observe the computing device received signaling.

Figure 8:
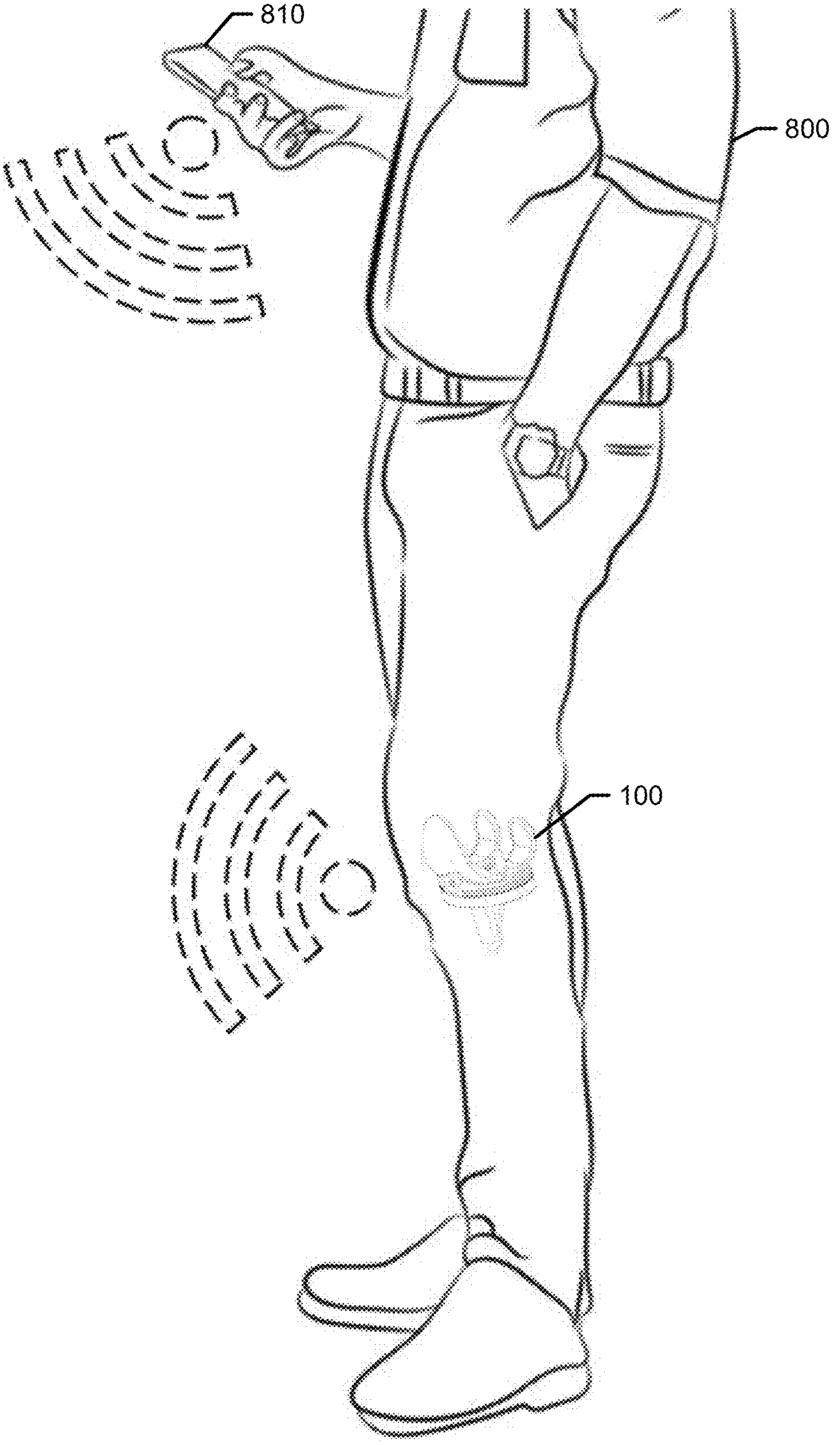
FIG. 8 illustrates a patient with the medical implant that is implanted in the patient and is configured to communication signaling to a mobile device of the patient, according to some embodiments of the present disclosure.

FIG. 8 illustrates a patient 800 with the medical implant 100 that is implanted in the patient 800 and is configured to communication signaling to a mobile device 810 of the patient 800, according to some embodiments of the present disclosure. The mobile device 810 may be a smart phone, computer, tablet, etc.

Figure 9:
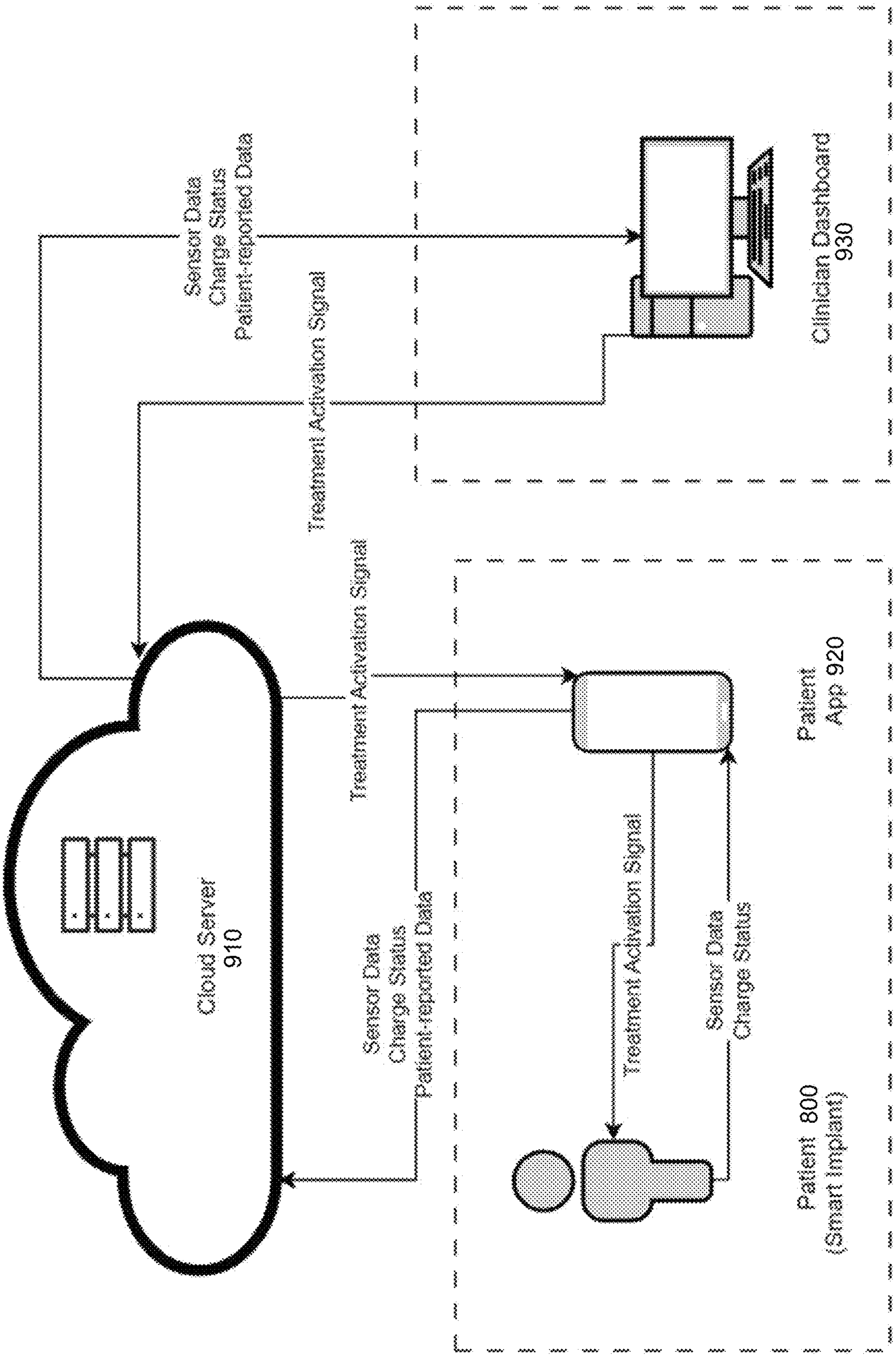
FIG. 9 illustrates a system that includes a cloud server, patient application, and clinician dashboard, according to some embodiments of the present disclosure.

FIG. 9 illustrates a system that includes a cloud server 810, patient application (also referred to as patient app) 920, and clinician dashboard 930, according to some embodiments of the present disclosure.

FIG. 9 shows the system of the present disclosure where in some embodiments, post-operatively, the medical implant senses the presence of bacterial biofilm on the surface of the medical implant components and transmits the sensor electrode readings to the clinician. The clinician decides on treatment based on sensor readings, information provided to the clinician through the accompanying patient app 920, and direct consultation. If the clinician determines that the patient has developed or is likely to develop an infection, the clinician can remotely activate a biofilm eradication program (electrical stimulation of the electrodes) on the patient's medical implant. The medical implant treatment may or may not be administered in combination with an antibiotic regimen. In addition, the clinician may also activate (through transmission from the computing device to the medical implant) a biofilm prevention program to prevent the formation of biofilm in the post-op recovery period of the index orthopedic procedure or following subsequent high-risk events such as dental procedures or urinary tract infections.

Referring to FIGS. 8 and 9, in some embodiments, the medical implant (e.g., medical implant 100) in patient 800 includes an implant component (e.g., implant component 150) configured to be implanted in patient 800. The medical implant may further include an electrode array (e.g., one of electrode arrays 120) comprising sensor electrodes spaced apart on the implant component. The medical implant may further include an energy storage device (e.g., energy storage device 130) inside the implant component and a wireless communication interface inside the implant component, configured to communicate with a wireless receiver that is separate from the medical implant. Additionally, the medical implant may include an implant circuitry (e.g., implant circuitry 156) inside the implant component and operative to supply voltage to at least one of the sensor electrodes to measure electrical and/or chemical characteristics and communicate signaling indicating the electrical and/or chemical characteristics through the wireless communication interface.

For example, the smart implant communicates with the patient's mobile phone 810, through the wireless communication interface, over a 2.4 GHz protocol such as Bluetooth® or Bluetooth® Low Energy (BLE). A mobile device compatible dongle may also be used to communicate to the wireless communication interface of the medical implant 100 on a radio frequency (RF) band that is not directly supported by the mobile device 810, such as 915 MHz or 401-406 MHz (MICS). The mobile device compatible dongle would contain transmission and receiver antenna(s) tuned to the target frequency of the medical implant communication protocol. In either scenario, the signaling is sent from patient's medical implant 100, received by the mobile device's integrated antenna or dongle's antenna, and then processed through a dedicated patient app 920 on the patient's mobile device 810.

In some embodiments, the electrical and/or chemical characteristics indicate at least one of impedance, conductivity, and potential hydrogen (pH).

In some embodiments, the implant circuitry is further operative to supply a defined range of frequencies, or a specific frequency, to the sensor electrodes to measure electrical and/or chemical characteristics. This may provide the benefit of measuring a range of frequencies in order to detect or measure a type of bacteria or biofilm that has a predetermined resonant/exultation frequency. Thus, the defined range of frequencies is adapted to electrically excite one or more types of bacterial species (targeted species that are particularly dangerous for PJI.

In some embodiments, one or more of the sensor electrodes is configured to detect presence of a type of bacterial species. In these embodiments, one or more sensor electrodes is coated with a bio-recognition element adapted to bind to the type of bacterial species.

In some embodiments, the electrode array includes a first zone (e.g., zone X of FIG. 6) of at least one sensor electrode of the sensor electrodes and a second zone (e.g., zone Y of FIG. 6) of at least one electrode of the sensor electrodes, wherein the first zone and second zone are separate. In these embodiments, the implant circuitry is further operative to compare the electrical and/or chemical characteristics from the at least one sensor electrode in the first zone to the electrical and/or chemical characteristics of the second zone, and generate the signaling to indicate the presence of a biofilm and/or indicate the electrical and/or chemical characteristics from the at least one sensor electrodes in the first zone and second zone, based on the electrical and/or chemical characteristics from the at least one sensor electrode in the first zone being a threshold difference from the electrical and/or chemical characteristics from the at least one sensor electrode in the second zone.

In some embodiments, the sensor electrodes include at least one of an oxygen sensor, impedance sensor, and a pH sensor.

In some embodiments, the signaling may further indicate a charge status of the medical implant. For example, the indication of the charge status may be a batter level of the energy storage device (e.g., energy storage device 130) or the implant component energy storage device (e.g., implant component energy storage device 154).

In some embodiments, the electrode array further includes stimulation electrodes spaced apart on the implant component, and the implant circuitry is further operative to electrically stimulate at least one of the stimulation electrodes by current supplied by the energy storage device to be at a level which reduces a biofilm on at least part of the implant component while implanted in the patient. The implant circuitry may control the current supplied by the energy storage device to the stimulation electrodes to be a level sufficient to form hydrogen bubbles through reaction with patient fluid and dislodge the biofilm and/or to change potential hydrogen (pH) of the patient fluid to a level which reduces the biofilm.

Additionally or alternatively, in some embodiments, the implant circuitry is further operative to simultaneously measure the electrical and/or chemical characteristics through the sensor electrodes and to electrically stimulate the stimulation electrodes. Additionally or alternatively, in some embodiments, the implant circuitry is further operative to increase or decrease the current supplied by the energy storage device to the stimulation electrodes responsive to the electrical and/or chemical characteristics.

By simultaneously measuring electrical and/or chemical characteristics through the sensor electrodes and electrically stimulating the stimulation electrodes, the electrical and/or chemical characteristics may be used as a feedback loop for determining if the biofilm has been reduced, removed from the medical implant or eliminated. Additionally, the electrical and/or chemical characteristics may be used as a feedback loop for determining if higher or lower current should be supplied to the stimulation electrodes, for example, to help increase the likelihood of removing or eliminating the biofilm. For example, the feedback loop may provide closed-loop control of current level used for stimulation so as to provide a highest current level within a defined range through selected stimulation electrode(s) to be used for removing a biofilm while monitoring sensor feedback from selected sensor electrode(s) to ensure pH remains in an acceptable range.

In some embodiments, the implant circuitry is further operative to determine presence of a biofilm based on the electrical and/or chemical characteristics, and generate the signaling to indicate the presence of the biofilm and/or indicate the electrical and/or chemical characteristics, based on the determined presence of the biofilm. Additionally or alternatively, in some embodiments, the implant circuitry is further operative to generate the signaling to further indicate locations on the implant component that correspond to where the electrical and/or chemical characteristics indicate the presence of the biofilm. Additionally or alternatively, in some embodiments, the electrode array further includes stimulation electrodes spaced apart on the implant component and the implant circuitry is further operative to electrically stimulate at least one of the stimulation electrodes on a part of the implant component associated with the biofilm by current supplied by the energy storage device to be at a level which reduces the biofilm.

In some embodiments, the electrode array further includes stimulation electrodes spaced apart on the implant component, and the implant circuitry is further operative to detect presence of the biofilm and/or a type of bacteria and a location of the biofilm and/or the type of bacteria based on the electrical and/or chemical characteristics, and stimulate the stimulation electrodes in the location based on the detected presence of the biofilm and/or the type of bacteria. The implant circuitry may be further operative to control the duration and/or level of stimulation of the stimulation electrodes based on the detected type of bacteria.

In some embodiments, the implant circuitry further includes a memory and is further operative to save the electrical and/or chemical characteristics to the memory and to generate the signaling to indicate values of the saved electrical and/or chemical characteristics. Additionally, the implant circuitry may compare the saved electrical and/or chemical characteristics over time and generate the signaling based on a threshold change in the saved electrical and/or chemical characteristics over a period of time. For example, saved electrical and/or chemical characteristics may indicate a pH level measured by a sensor electrode. Over a period of time if the sensor electrode measures a threshold change (e.g., a threshold increase in the pH level), then the implant circuitry may generate the signaling based on this threshold change occurring.

In some embodiments, the electrode array further includes at least one reference electrode (e.g., reference electrode 420), and the implant circuitry is further operative to supply voltage to the at least one reference electrode while measuring electrical and/or chemical characteristics through the reference electrode, and communicate signaling indicating the electrical and/or chemical characteristics through the at least one reference electrode through the wireless communication interface. Additionally or alternatively, in some embodiments, the implant circuitry is further operative to compare the electrical and/or chemical characteristics through the at least one reference electrode and the electrical and/or chemical characteristics through the sensor electrodes, and generate the signaling to indicate the presence of the biofilm and/or indicate the electrical and/or chemical characteristics through the at least one reference electrode and the sensor electrodes, based on the electrical and/or chemical characteristics through the at least one reference electrode having at least a threshold difference from the electrical and/or chemical characteristics through the sensor electrodes.

In some embodiments, the signaling is sent from the mobile device 810 to the cloud server 910. The signaling from the mobile device to the cloud server may include at least the electrical and/or chemical characteristics, the charge status of the energy storage device, and some patient reported data (e.g., information a patient inputs into the patient app 920). For example, the data from the app (including indications in the signaling) may be uploaded from the patient's mobile device 810 to a secure cloud server 910 via internet connection such as WiFi or cellular communications such as 5G or LTE. Data may be processed on the patient's mobile device 810 prior to upload or on the cloud server 910 after upload. After processing, the data can then be accessed by the patient 800 via their patient app 920 and by the clinician via a dedicated clinician dashboard 930.

It is noted that the mobile device 810 may alternatively be a relay device or a power transmission device (e.g., power transmission device of FIGS. 10 and 11) that is used to receive the signaling from the wireless communication interface of the medical implant and transmit the signaling to a computing device for the clinician to view the signaling and generate commands regarding treatment or other control of the medical device. The clinician dashboard 930 may be displayed to the clinician on the computing device.

In some embodiments, the computing device includes a wireless communication interface operative to receive, from the medical implant, signaling based on the measured electrical and/or chemical characteristics through the sensor electrodes spaced apart on the component of the medical implant. The computing device may further include circuitry operative to detect presence of a biofilm and a location of the biofilm on the medical implant based on the received signaling, and transmit a message (e.g., treatment activation signal) that identifies stimulation electrodes, that are associated with the determined location of the biofilm, on the medical implant that are to be stimulated by current supplied by the implant circuitry to be at a level which reduces the biofilm.

In some embodiments, the location of the biofilm may be indicated by (correspond to) a zone in an electrode array, an electrode array, and/or a placement of the electrode array on a component of the medical implant.

In some embodiments, the circuitry of the computing device is further operative to generate the message to indicate duration and/or level of stimulation for the identified stimulation electrodes based on the received electrical and/or chemical characteristics.

In some embodiments, the circuitry of the computing device is further operative to detect the presence of the biofilm based on a trend over time of the received electrical and/or chemical characteristics. For example, the circuitry may detect the presence of the biofilm based on a pH level and/or impedance changing over time.

In some embodiments, the circuitry is further operative to determine a type of bacteria in the biofilm based on the signaling from the medical implant. The circuitry can determine duration and/or level of stimulation based on the determined type of bacteria, and can generate the message to indicate the duration and/or level of stimulation for the identified stimulation electrodes.

For example, the message (e.g., a treatment activation signal), that identifies at least one of the stimulation electrodes of the medical implant to be electrically stimulated, may be uploaded to the cloud server 910 and then accessed or obtained by the mobile device 810. The mobile device may then transmit the message to the medical device.

However, it should be noted that in some embodiments, the implant circuitry may be operative to perform the operations of the computing device.

In some embodiments, the electrode array of the medical implant further includes stimulation electrodes spaced apart on the implant component, and the implant circuitry is further operative to receive the message, through the wireless communication interface, identifying at least one of the stimulation electrodes to be electrically stimulated, and electrically stimulate the at least one of the stimulation electrodes identified by the received message.

Figure 10:
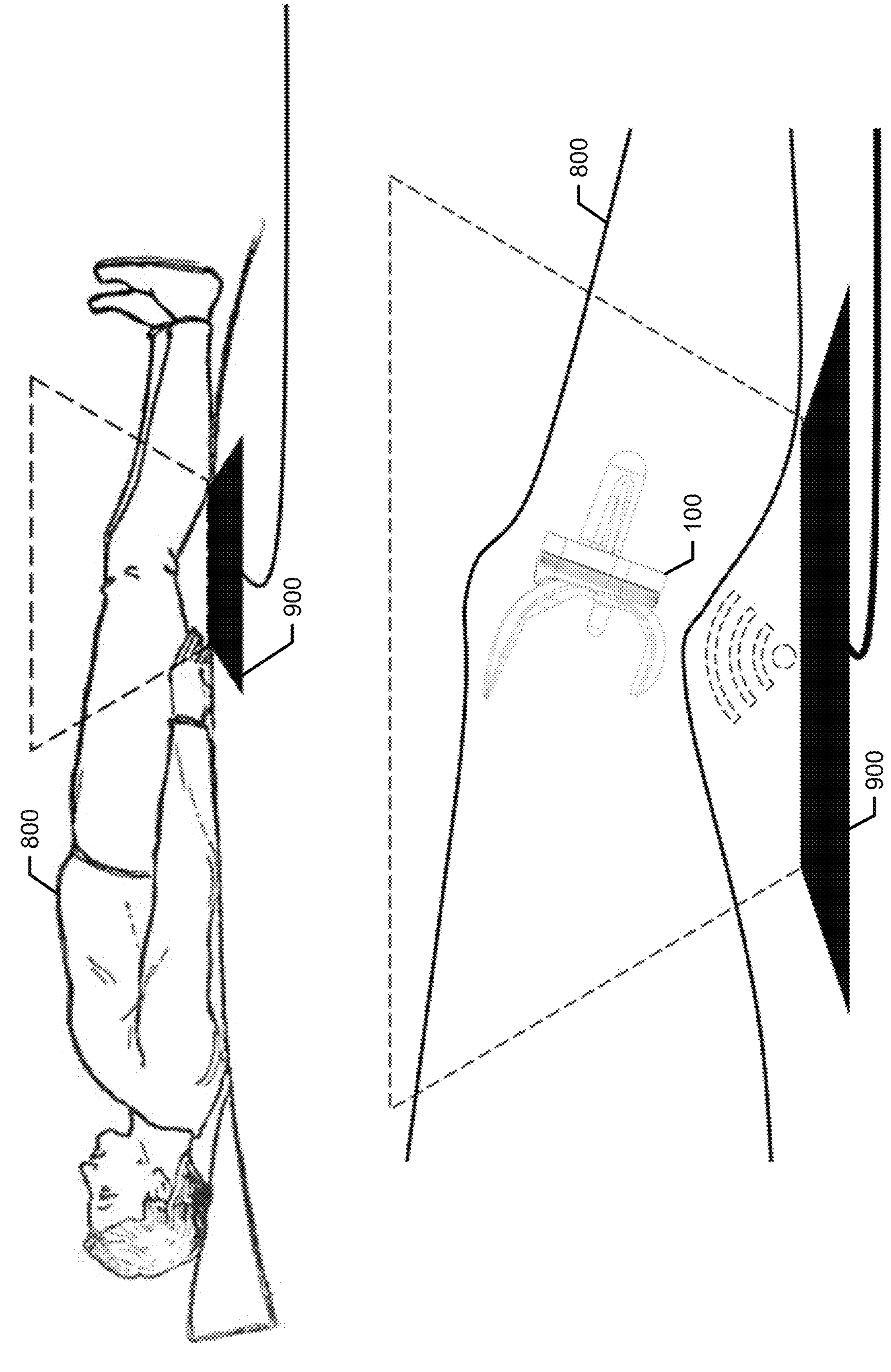
FIG. 10 illustrates the patient with the medical implant that is implanted in the patient and is configured to wirelessly receive radio frequency (RF) signals from a power transmitter device and charge the energy storage device from the received RF signals, according to some embodiments of the present disclosure.

FIG. 10 illustrates the patient 800 with the medical implant 100 that is implanted in the patient 800 and is configured to wirelessly receive radio frequency (RF) signals from a power transmitter device 900 and charge the energy storage device (e.g., energy storage device 130) of the medical implant from the received RF signals, according to some embodiments of the present disclosure.

Figure 11:
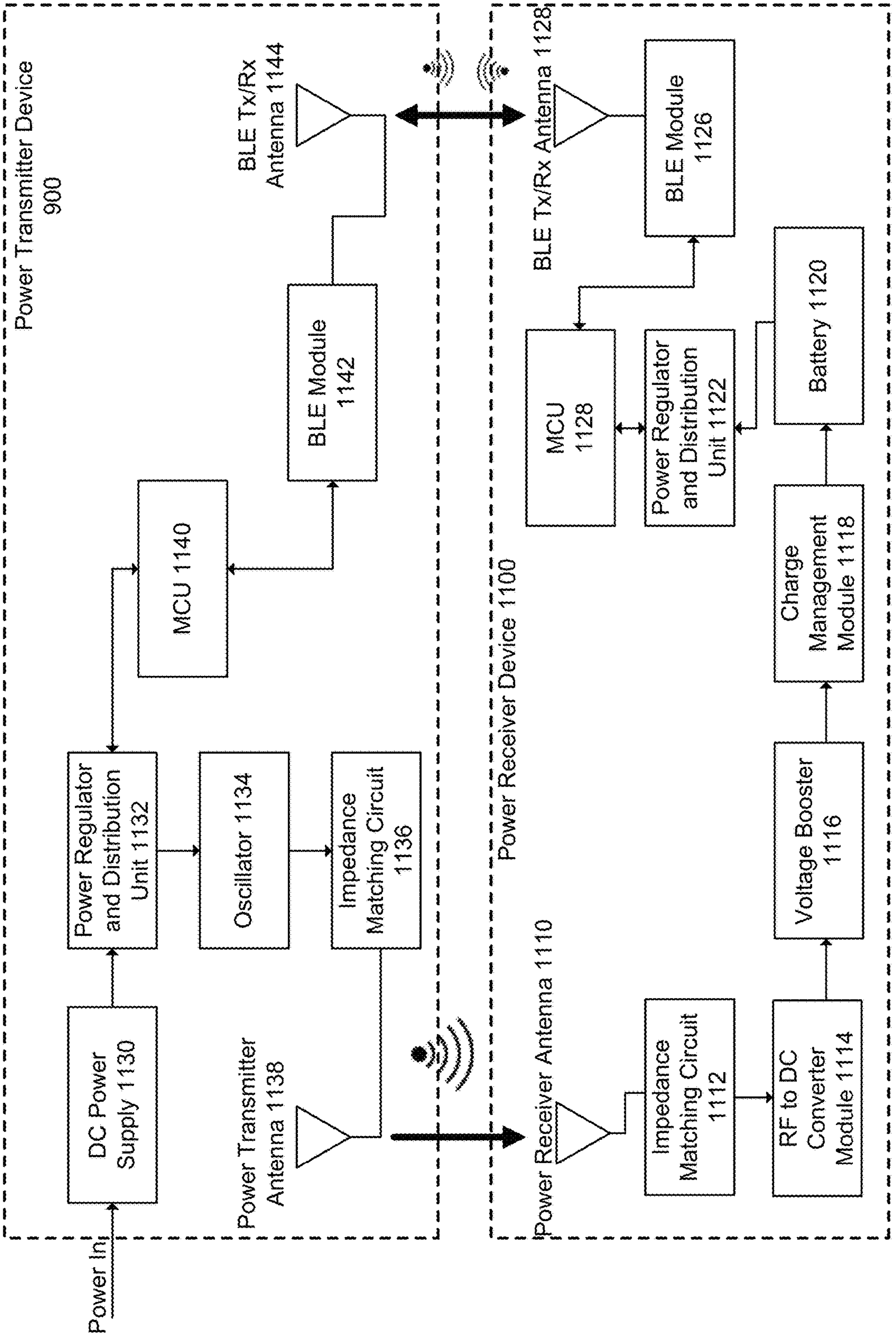
FIG. 11 illustrates a block diagram of a power receiver device of the medical implant and a power transmitter device where the power receiver device is configured to receive, from the power transmitter device, RF signals to allow for wireless charging of the medical implant and receive/transmit other signals to the power transmitter device, according to some embodiments of the present disclosure.

FIG. 11 illustrates a block diagram of a power receiver device 1100 of the medical implant and the power transmitter device 900 where the power receiver device 1100 is configured to receive, from the power transmitter device 900, RF signals to allow for wireless charging of the medical implant and receive/transmit other signals to the power transmitter device 900, according to some embodiments of the present disclosure In some embodiments, a power receiver circuitry (e.g., power receiver device 1100) that wirelessly receives radio frequency (RF) signals from a power transmitter device (e.g., power transmitter device 900) that is separate from the medical implant 100, converts the received RF signals to direct current (DC) power, and charges the energy storage device (e.g., energy storage device 130) with the DC power.

Referring to the examples of FIGS. 10 and 11, the medical implant 100 is powered by an integrated rechargeable battery (e.g., energy storage device 130). The battery is recharged via an automated RF-based wireless charging system. The charging system includes a power receiver device 1100 embedded within the medical implant and an power transmitter device 900.

The power transmitter device 900 contains a signal antenna (e.g., BLE Transmission (Tx)/Reception (Rx) Antenna 1144) and power transmitter antenna 1138, which may operate on the same or different frequencies. For example, the signal antenna might operate at 2.4 GHz to facilitate communication with the medical implant and mobile device via Bluetooth® while the power transmitter antenna 1138 operates at 915 MHz. The signal antenna and power transmitter antenna 1138 are connected to a microcontroller (MCU) 1140 or other processor unit within the device.

In some embodiments the electronic components of the power transmitter device 900 are housed in a pad-like form factor to enable the patient 800 to place the power transmitter device 900 on top of their mattress or preferred seating area. The antennas within the power transmitter device 900 are designed for directional transmission normal to the plane of the pad as shown by the dotted lines in FIG. 10. Additionally, the antennas form a coverage volume to facilitate charging of the medical implant while the patient 800 is lying down or seated in various positions.

The medical implant may include a signal antenna (e.g., BLE Tx/Rx antenna 1128) and power receiver antenna 1110, which may operate on the same or different frequencies. For example, the signal antenna might operate at 2.4 GHz to facilitate communication with the power transmitter device 900 and mobile device (e.g., mobile device 810) via Bluetooth® while the power receiver antenna 1110 operates at 915 MHz. Power received by the power receiver antenna 1110 is converted to DC and then passed to a charging module to charge the battery (discussed in more detail below).

In some embodiments, the power receiver device 1100 of the medical implant is within the implant component (e.g., implant component 150) or is separate from the implant component.

In other embodiments, the electronic components of the power transmitter device 900 are housed in a medical brace-like form factor (e.g., a knee brace, leg brace, wrist brace, etc) to enable the patient to wear the power transmitter device 900.

In preferred embodiments, the power transmitter device 900 receives power from a wall outlet, however, in some embodiments the power transmitter device 900 also includes a battery that allows the power transmitter device 900 to be more mobile and receive the power from the battery.

Referring to FIG. 11, for power transfer from the power transmitter device 900 to the power receiver device 1100, the DC power supply 1130 receives power from an external power source (e.g., wall outlet) and sends the power to a power regulator and distribution unit 1132. The power regulator and distribution unit 1132 regulates the power received by the power transmitter device 900 and distributes the power to a MCU 1140 and/or oscillator 1134. The oscillator 1134 oscillates the power into a signal (e.g., RF signal) and sends the signal to an impedance matching circuit 1136 that performs impedance matching operations to help maximize the power transfer to the power receiver device 1100. The impedance matching circuit then sends the impedance matched signal (through power transmitter antenna 1138) to a power receiver antenna 1110 of the power received device 1100.

The power receiver antenna 1110 receives the power signal and sends the power signal to the impedance matching circuit 1112, which then sends the signal to a RF to DC converter module 1114. The RF to DC converter module 1114 converts the power signal from RF signals to DC power and sends this DC power to the voltage booster 1116. The voltage booster 1116 boosts the DC power voltage and sends the voltage boosted DC power to the charge management module 1118, which then sends the power to the battery 1120.

For communications (e.g., BLE communications) from the power transmitter device 900 to the power receiver device 1100, the MCU 1140 receives power from the power regulator and distribution unit 1132 and sends signals (e.g., treatment activation signal(s)) to the BLE module 1142, which sends signals (through the BLE Tx/Rx antenna 1144) to a BLE Tx/Rx antenna 1128 of the power receiver device 1100.

For communications (e.g., BLE communications) from the power receiver device 1100 to the power transmitter device 900, the battery 1120 sends power to the power regulator and distribution unit 1122, which then sends the power to the MCU 1128. The MCU 1128 sends a signal(s) (e.g., signaling indicating electrical and/or chemical characteristics) to the BLE module 1126 which transmits, through the BLE Tx/Rx antenna 1128 the signal(s) to the BLE Tx Rx antenna 1144 of the power transmitter device 900.

In some embodiments, the power transmitter device 900 may act as a relay device that receives these signals from the power receiver device 1100 or another wireless communication interface and upload the signals to a cloud server (e.g., cloud server 910 of FIG. 9).

Figure 13:
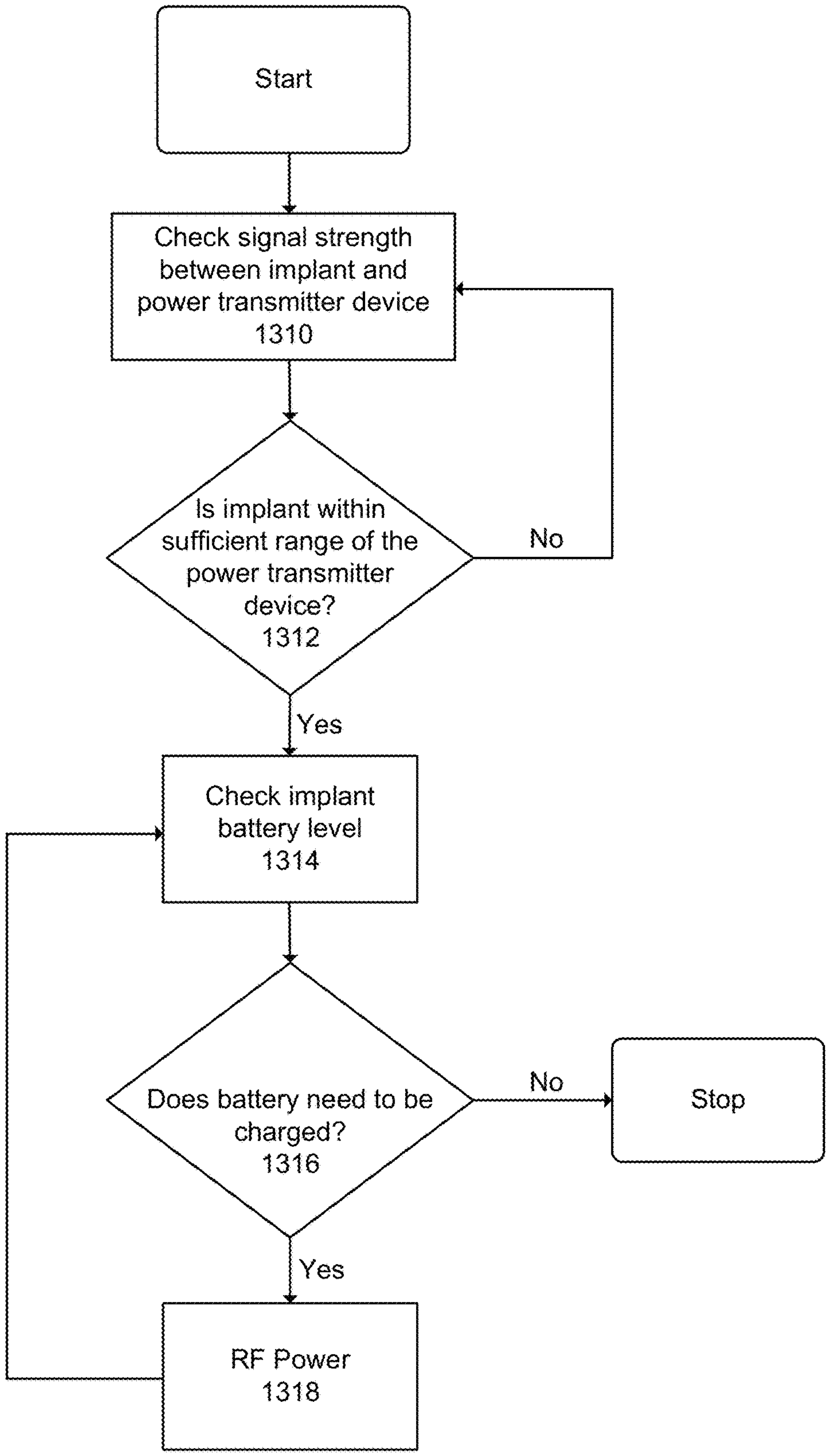
FIG. 13 illustrates a block diagram of wireless charging operations performed by the medical implant and/or power transmitter device, according to some embodiments of the present disclosure.

FIG. 13 illustrates a block diagram of wireless charging operations performed by the medical implant and/or power transmitter device, according to some embodiments of the present disclosure. In some embodiments, the operations are performed by the medical implant (e.g., implant circuitry 156). In other embodiments, the operations are performed by the MCU 1140 of the power transmitter device 900.

The operation of FIG. 13 are directed to an automated charging algorithm that recharges the energy storage device of the medical implant as needed without intervention from the patient. The patient may only need to ensure that the power transmitter device is plugged into a wall outlet for power.

When the medical implant performs the operations of FIG. 13, in operation 1310, the medical implant checks the signal strength between the medical implant and the power transmitter device. The medical implant then, in operation 1312, determines if the implant is within sufficient range of the power transmitter device. If not within sufficient range, then the medical implant returns to operation 1310. If the medical implant is within sufficient range, then the medical implant moves to operation 1314. In operation 1314, the medical implant checks the medical implant's battery level. The medical implant then, in operation 1316, determines if the battery needs to be charged. This determination may be based on the medical implant's batter level being below a threshold value. If the medical implant determines that the battery does not need to be charged, the medical implant stops the operations of FIG. 13. If the medical implant determines that the battery needs to be charged, then the medical implant moves to operation 1318 and receives RF power transmissions from the power transmitter device. As the medical implant receives the RF power transmission, the medical implant (at least periodically) performs operations 1314 through 1318.

When the power transmitter device performs the operations of FIG. 13, in operation 1310, the power transmitter device checks the signal strength between the medical implant and the power transmitter device. Then, in operation 1312, the power transmitter device determines if the medical implant is within sufficient range of the power transmitter device. If the medical implant is not within sufficient range, then the power transmitter returns to operation 1310. If the medical implant is within sufficient range, the power transmitter moves to operation 1314. In operation 1314, the power transmitter device checks the medical implant's batter level by transmitting a batter level request to the medical implant and the power transmitter receiving a battery level response from the medical implant that includes an indication of the medical implant's battery level. Then in operation 1316, the power transmitter device determines if the battery of the medical implant needs to be charged. If the battery does not need to be charged, then the operations of FIG. 13 stop. If the battery needs to be charged, then the power transmitter device moves to operation 1318, where the power transmitter device then transmits RF power to the medical implant. As the power transmitter device transmits the RF power, the power transmitter device (at least periodically) performs operations 1314 through 1318.

Figure 12:
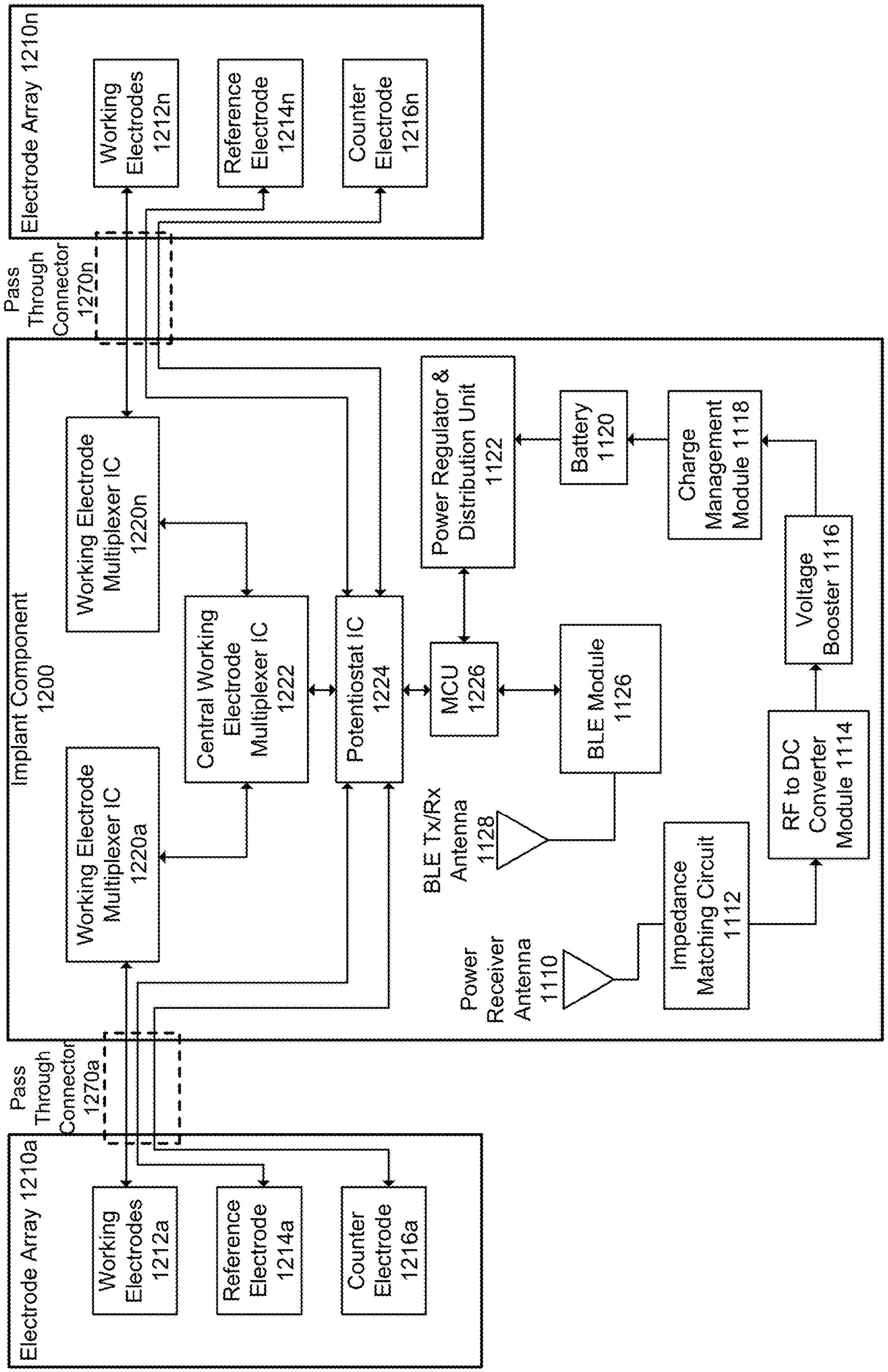
FIG. 12 illustrates components of the implant component and communications to/from the electrode arrays of the implant component, according to some embodiments of the present disclosure.

FIG. 12 illustrates components of the implant component and communications to/from the electrode arrays of the implant component, according to some embodiments of the present disclosure.

The illustrated configuration of FIG. 12 includes one or more electrode arrays (electrode arrays 1210*a-n*) on the surface of the implant component. Each electrode array may include one or more working electrodes (e.g., working electrodes 1212*a-n*), a reference electrode (e.g., reference electrode 1214*a-n*), and a counter electrode (e.g., counter electrode 1216*a-n*). Each electrode is electrically connected to the implant component via pass through connectors at an interface of the implant component. Working Electrodes 1212*a-n* are internally routed to a dedicated multiplexer integrated circuit (IC) 1220*a-n*. For configurations involving more than one electrode array, each electrode array may have a dedicated multiplexer that is connected to a central multiplexer (central working electrode multiplexer IC 1222). The central working electrode multiplexer IC 1222 is connected to the potentiostat IC 1224, which performs the electrochemical signal output and processing of signal responses. The multiplexers enable switching of connections between individual working electrodes and the single potentiostat IC 1224. Otherwise an individual potentiostat IC would be required for each working electrode. The reference and counter electrodes of each electrode array may also be connected to the potentiostat IC to complete the 3-electrode system. The potentiostat IC is connected to the MCU 1226, which may be the primary processor for the entire system. The remaining power and communication elements of the implant component are described with reference to Figure above.

While a single potentiostat IC is used herein, a plurality of potentiostat may be used. For example, there may be a potentiostat IC for each electrode array.

The implant component of FIG. 12 may also be used to deliver electric stimulation to prevent and/or eradicate biofilm on the surface of the medical implant. In general, a potentiostat is the electronic hardware required to control a three-electrode cell for electrochemical experiments. Depending on the application, a potentiostat can be used to supply constant DC current or constant DC voltage to the electrodes. In electrochemical impedance spectroscopy applications, a potentiostat can also be used to supply AC potential at a fixed frequency or across a defined range of frequencies. Each of these potentiostat modalities could be used to supply AC and/or DC electric stimulation to the electrodes on the surface of the medical implant. Rather than supplying signals and recording the results as in electrochemical sensing, the focus of electric stimulation may be on the output signal from the circuit. In some embodiments, the same sets and arrays of electrodes used in measuring electrical and/or chemical characteristics may be used for electric stimulation. In some alternative embodiments, the implant component may include dedicated arrays, sets, or individual electrodes for the purpose of stimulation.

One possible clinical application of electric stimulation is to generate controlled concentrations of biocidal molecules, such as HOCl (hypochlorous acid), at electrode surfaces beneath or adjacent to bacterial biofilms on the medical implant. HOCl is naturally produced by white blood cells when combatting bacteria in humans and is commonly used as a wound cleansing agent in clinical settings. In low, controlled concentrations HOCl can kill bacteria and eradicate bacterial biofilms without cytotoxic effects to the surrounding tissue. In one embodiment, the medical implant could stimulate the electrodes on the surface of the implant at a constant voltage between 1.2V to 1.7V to generate low concentrations (1-50 uM) of HOCl at the interface of the electrodes and synovial fluid and/or electrodes and biofilm. The stimulation could be applied for a fixed amount of time, such as 1-3 hours, or until the sensor electrodes no longer detect the presence of the biofilm. In addition, some electrodes in the electrode array may be configured to measure the concentration of HOCl. These electrodes may be used to create an additional feedback loop (as similarly discussed above) to precisely control the concentration of generated HOCl to remain below cytotoxic limits. This feedback loop may also be used to ensure that a sufficient concentration of HOCl is generated as the concentration of chloride ions and pH level may impact the voltage required to achieve the target HOCl concentration.

FURTHER DEFINITIONS AND EMBODIMENTS

It should be noted that the use of the term "characteristic" and "parameter" may be used interchangeably.

In the above-description of various embodiments of present inventive concepts, it is to be understood that the terminology used herein is for the purpose of describing particular embodiments only and is not intended to be limiting of present inventive concepts. Unless otherwise defined, all terms (including technical and scientific terms) used herein have the same meaning as commonly understood by one of ordinary skill in the art to which present inventive concepts belongs. It will be further understood that terms, such as those defined in commonly used dictionaries, should be interpreted as having a meaning that is consistent with their meaning in the context of this specification and the relevant art and will not be interpreted in an idealized or overly formal sense expressly so defined herein.

When an element is referred to as being "connected", "coupled", "responsive", or variants thereof to another element, it can be directly connected, coupled, or responsive to the other element or intervening elements may be present. In contrast, when an element is referred to as being "directly connected", "directly coupled", "directly responsive", or variants thereof to another element, there are no intervening elements present. Like numbers refer to like elements throughout. Furthermore, "coupled", "connected", "responsive", or variants thereof as used herein may include wirelessly coupled, connected, or responsive. As used herein, the singular forms "a". "an" and "the" are intended to include the plural forms as well, unless the context clearly indicates otherwise. Well-known functions or constructions may not be described in detail for brevity and/or clarity. The term "and/or" includes any and all combinations of one or more of the associated listed items.

It will be understood that although the terms first, second, third, etc. may be used herein to describe various elements/operations, these elements/operations should not be limited by these terms. These terms are only used to distinguish one element/operation from another element/operation. Thus, a first element/operation in some embodiments could be termed a second element/operation in other embodiments without departing from the teachings of present inventive concepts. The same reference numerals or the same reference designators denote the same or similar elements throughout the specification.

As used herein, the terms "comprise", "comprising", "comprises", "include", "including", "includes", "have", "has", "having", or variants thereof are open-ended, and include one or more stated features, integers, elements, steps, components or functions but does not preclude the presence or addition of one or more other features, integers, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

Example embodiments are described herein with reference to block diagrams and/or flowchart illustrations of computer-implemented methods, apparatus (systems and/or devices) and/or computer program products. It is understood that a block of the block diagrams and/or flowchart illustrations, and combinations of blocks in the block diagrams and/or flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and/or flowchart block or blocks, and thereby create means (functionality) and/or structure for implementing the functions/acts specified in the block diagrams and/or flowchart block(s).

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and/or flowchart block or blocks. Accordingly, embodiments of present inventive concepts may be embodied in hardware and/or in software (including firmware, resident software, microcode, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Finally, other blocks may be added/inserted between the blocks that are illustrated, and/or blocks/operations may be omitted without departing from the scope of inventive concepts. Moreover, although some of the diagrams include arrows on communication paths to show a primary direction of communication, it is to be understood that communication may occur in the opposite direction to the depicted arrows.

Many variations and modifications can be made to the embodiments without substantially departing from the principles of the present inventive concepts. All such variations and modifications are intended to be included herein within the scope of present inventive concepts. Accordingly, the above disclosed subject matter is to be considered illustrative, and not restrictive, and the appended examples of embodiments are intended to cover all such modifications, enhancements, and other embodiments, which fall within the spirit and scope of present inventive concepts. Thus, to the maximum extent allowed by law, the scope of present inventive concepts are to be determined by the broadest permissible interpretation of the present disclosure including the following examples of embodiments and their equivalents, and shall not be restricted or limited by the foregoing detailed description.

What is claimed is:

1. A medical implant comprising:

an implant component configured to be implanted in a patient;

an electrode array comprising sensor electrodes spaced apart on the implant component;

an energy storage device within the implant component;

a wireless communication interface within the implant component, configured to communicate with a wireless receiver that is separate from the medical implant; and implant circuitry within the implant component and operative to supply voltage to at least one of the sensor electrodes to measure electrical and/or chemical characteristics associated with when a biofilm is forming on the implant component, and communicate signaling indicating the electrical and/or chemical characteristics through the wireless communication interface, wherein the electrode array further comprises stimulation electrodes spaced apart on the implant component, and the implant circuitry is further operative to electrically stimulate at least one of the stimulation electrodes by current supplied by the energy storage device to be at a level which reduces the biofilm on at least part of the implant component while implanted in the patient, and wherein the implant circuitry is further operative to control the current supplied by the energy storage device to the stimulation electrodes to be a level sufficient to form hydrogen bubbles through reaction with patient fluid and dislodge the biofilm and/or to change potential hydrogen (PH) of the patient fluid to a level which reduces the biofilm.

2. The medical implant of claim 1, wherein:

the implant circuitry is further operative to determine presence of the biofilm based on the electrical and/or chemical characteristics, and generate the signaling to indicate the presence of the biofilm and/or indicate the electrical and/or chemical characteristics, based on the determined presence of the biofilm.

3. The medical implant of claim 2, wherein:

the implant circuitry is further operative to generate the signaling to further indicate locations on the implant component that correspond to where the electrical and/or chemical characteristics indicate the presence of the biofilm.

4. The medical implant of claim 2, wherein:

the electrode array further comprises stimulation electrodes spaced apart on the implant component, and the implant circuitry is further operative to electrically stimulate at least one of the stimulation electrodes on a part of the implant component associated with the biofilm by supplying current from the energy storage device at a level which reduces the biofilm.

5. The medical implant of claim 1, wherein:

the electrode array further comprises stimulation electrodes spaced apart on the implant component, and the implant circuitry is further operative to receive a message through the wireless communication interface identifying at least one of the stimulation electrodes to be electrically stimulated, and electrically stimulate the at least one of the stimulation electrodes identified by the message.

6. The medical implant of claim 1, wherein:

the electrode array further comprises stimulation electrodes spaced apart on the implant component, and the implant circuitry is further operative to detect a location of the biofilm and/or the type of bacteria in the biofilm based on the electrical and/or chemical characteristics, and stimulate the stimulation electrodes in the location based on the detected presence of the biofilm and/or based on the detected type of bacteria.

7. The medical implant of claim 6, wherein:

the implant circuitry is further operative to control the duration and/or level of stimulation of the stimulation electrodes based on the detected type of bacteria.

8. The medical implant of claim 1, wherein:

the implant circuitry further comprises a memory and is further operative to save data in the memory indicating the electrical and/or chemical characteristics and to generate the signaling to indicate values of the saved data indicating the electrical and/or chemical characteristics.

9. The medical implant of claim 1, further comprising:

a power receiver circuitry that wirelessly receives radio frequency (RF) signals from a power transmitter device that is separate from the medical implant, converts the received RF signals to direct current (DC) power, and charges the energy storage device with the DC power.

10. The medical implant of claim 1, wherein:

the electrical and/or chemical characteristics indicate at least one of impedance, conductivity, and potential hydrogen (pH).

11. The medical implant of claim 1, wherein:

the implant circuitry is further operative to simultaneously measure the electrical and/or chemical characteristics through the sensor electrodes and to electrically stimulate the stimulation electrodes.

12. The medical implant of claim 11, wherein:

the implant circuitry is further operative to increase or decrease the current supplied by the energy storage device to the stimulation electrodes responsive to the electrical and/or chemical characteristics.

13. The medical implant of claim 1, wherein:

the electrode array further comprises at least one reference electrode, and the implant circuitry is further operative to supply voltage to the at least one reference electrode while measuring electrical and/or chemical characteristics through the reference electrode, and communicate signaling indicating the electrical and/or chemical characteristics through the at least one reference electrode through the wireless communication interface.

14. The medical implant of claim 13, wherein:

the implant circuitry is further operative to compare the electrical and/or chemical characteristics through the at least one reference electrode and the electrical and/or chemical characteristics through the sensor electrodes, and generate the signaling to indicate the presence of the biofilm and/or indicate the electrical and/or chemical characteristics through the at least one reference electrode and the sensor electrodes, based on the electrical and/or chemical characteristics through the at least one reference electrode having at least a threshold difference from the electrical and/or chemical characteristics through the sensor electrodes.

15. The medical implant of claim 1, wherein:

one of the sensor electrodes is configured to detect presence of a type of bacterial species.

16. The medical implant of claim 15, wherein:

the one of the sensor electrodes is coated with a biorecognition element adapted to bind to the type of bacterial species.

17. The medical implant of claim 1, wherein:

the implant circuitry is further operative to supply a defined range of frequencies to the sensor electrodes to measure electrical and/or chemical characteristics, wherein the defined range of frequencies is adapted to electrically excite one or more types of bacterial species.

18. The medical implant of claim 1, wherein:
the electrode array comprises a first zone of at least one sensor electrode of the sensor electrodes and a second zone of at least one electrode of the sensor electrodes, wherein the first zone and second zone are separate, and
the implant circuitry is further operative to
compare the electrical and/or chemical characteristics from the at least one sensor electrode in the first zone to the electrical and/or chemical characteristics of the second zone, and
generate the signaling to indicate the presence of the biofilm and/or indicate the electrical and/or chemical characteristics from the at least one sensor electrodes in the first zone and second zone, based on the electrical and/or chemical characteristics from the at least one sensor electrode in the first zone being a threshold difference from the electrical and/or chemical characteristics from the at least one sensor electrode in the second zone.

* * * * *